US012617755B2

(12) United States Patent
Church et al.

(10) Patent No.: US 12,617,755 B2
(45) Date of Patent: May 5, 2026

(54) COMPOSITIONS AND METHODS FOR TREATING METABOLIC DISEASE

(71) Applicant: The Regents of the University of California, Oakland, CA (US)

(72) Inventors: Arpana Church, Los Angeles, CA (US); Tien Dong, Los Angeles, CA (US); Emeran A. Mayer, Los Angeles, CA (US); Jonathan P. Jacobs, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 1058 days.

(21) Appl. No.: 17/633,811

(22) PCT Filed: Aug. 3, 2020

(86) PCT No.: PCT/US2020/044749

§ 371 (c)(1),
(2) Date: Feb. 8, 2022

(87) PCT Pub. No.: WO2021/030091

PCT Pub. Date: Feb. 18, 2021

(65) Prior Publication Data

US 2022/0298111 A1 Sep. 22, 2022

Related U.S. Application Data

(60) Provisional application No. 62/885,010, filed on Aug. 9, 2019.

(51) Int. Cl.

| | |
|---|---|
| ***C07D 209/08*** | (2006.01) |
| ***A23L 33/10*** | (2016.01) |
| ***A23L 33/135*** | (2016.01) |
| ***A61P 3/04*** | (2006.01) |

(52) U.S. Cl.

CPC ............ *C07D 209/08* (2013.01); *A23L 33/10* (2016.08); *A23L 33/135* (2016.08); *A61P 3/04* (2018.01)

(58) Field of Classification Search

CPC ........... C12R 2001/01; C12R 2001/145; A23L 33/10; A23L 33/135; A61P 3/04; A61K 2035/115; A61K 35/742; A61K 31/405; A61K 35/741; C07D 209/08; C07D 209/18; C07D 307/79; C07D 333/60; C12N 1/20

See application file for complete search history.

(56) References Cited

U.S. PATENT DOCUMENTS

2013/0224155 A1* 8/2013 Kaplan .................. A61P 25/28
435/6.12

FOREIGN PATENT DOCUMENTS

| | | | |
|---|---|---|---|
| WO | WO-2011/140488 | A1 | 11/2011 |
| WO | WO-2013/130773 | A2 | 9/2013 |
| WO | WO-2016/070151 | A1 | 5/2016 |
| WO | WO-2018/136884 | A1 | 7/2018 |
| WO | WO-2018/229193 | A1 | 12/2018 |
| WO | WO-2019/046646 | A1 | 3/2019 |
| WO | WO-2021/030091 | A1 | 2/2021 |

OTHER PUBLICATIONS

Chavez-Carbajal et al., "Gut microbiota and predicted metabolic pathways in a sample of Mexican women affected by obesity and obesity plus metabolic syndrome," International Journal of Molecular Sciences, 20(2): 438 (18 pages) (2019).
Dong et al., "A Distinct Brain-Gut-Microbiome Profile Exists for Females with Obesity and Food Addiction," 28(8): 1477-1486 (2020).
Everard et al., "Cross-talk between Akkermansia muciniphila and intestinal epithelium controls diet-induced obesity," PNAS, 110(22): 9066-9071 (2013).
International Search Report and Written Opinion for International Application No. PCT/US2020/044749 dated Nov. 16, 2020.
Jin et al., "2-Aminomethyl piperidines as novel urotensin-II receptor antagonists," Bioorganic & Medicinal Chemistry Letters, 18(9): 2860-2864 (2008).
Stanislawski et al., "Gut microbiota phenotypes of obesity," NPJ Biofilms and Microbiomes, 5(1): 18 (9 pages) (2019).
Nistal et al., "Changes of the Gut Microbiota in Patients with Obesity, Metabolic Syndrome and Non-Alcoholic Fatty Liver Disease versus Healthy Controls," Journal of Hepatology, 64(2): S490 (2016).
Extended European Search Report for EP Application No. 20851887.8 dated Oct. 16, 2023.
Partial European Search Report for EP Application No. 20851887.8 dated Jul. 14, 2023.

* cited by examiner

*Primary Examiner* — Sahar Javanmard
(74) *Attorney, Agent, or Firm* — Foley Hoag LLP; David P. Halstead; Alexander J. Chatterley

(57) ABSTRACT

The present disclosure relates to compounds, compositions and supplements that are capable of treating obesity. The disclosure further relates to methods of treating obesity in a subject in need thereof.

15 Claims, 22 Drawing Sheets

COMPOSITIONS AND METHODS FOR TREATING METABOLIC DISEASE

RELATED APPLICATIONS

This application is the § 371 U.S. National-Stage application of PCT/US2020/044749, filed Aug. 3, 2020, which claims the benefit of U.S. Provisional Patent Application No. 62/885,010, filed on Aug. 9, 2019. The contents of each of these applications are hereby incorporated by reference in their entirety.

GOVERNMENT SUPPORT

This invention was made with government support under DK048351, DK041301, DK121025, DK007180, DK106528 and TR001881, awarded by the National Institutes of Health. The government has certain rights in the invention.

BACKGROUND

Obesity has reached global epidemic proportions and has become one of the leading preventable causes of death in the United States, for example in 2008, an estimated 500 million adults worldwide were considered obese. Obesity is associated with many comorbidities, such as diabetes, cancer(s), premature mortality from cardiovascular disease (CVD), and musculoskeletal disorders.

In addition to the health detriments, the economic and social consequences of obesity are compounding. For instance, in 2011, medical costs associated with treatment of preventable diseases associated with obesity were estimated to increase by $48-66 billion/year in the U.S. alone, with an estimated 65 million more adults to become obese by 2030.[5] Accordingly, there is an ongoing need for new treatments for obesity.

SUMMARY OF THE INVENTION

Provided herein are compounds, compositions, food supplements and methods for treating obesity and/or food addiction. In one aspect, the present disclosure provides compounds of formula I:

I

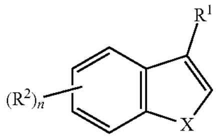

or a pharmaceutically acceptable salt thereof, wherein

X is O, $NR^3$, or S;

$R^1$ is alkyl, wherein the alkyl is optionally substituted, e.g., with hydroxyl, thio, sulfonamido, carbamate, carboxy, ester, or amido;

each $R^2$ is independently selected from alkyl, halo, hydroxyl, carboxyl, acyl, ester, thioester, alkoxy, phosphoryl, amino, amido, cyano, nitro, azido, alkylthio, alkenyl, alkynyl, cycloalkyl, heterocyclylalkyl, heteroaralkyl, sulfonamide, aryl, heteroaryl, heterocyclyl, and aralkyl;

$R^3$ is hydrogen or alkyl; and n is 0-4.

In another aspect, the present disclosure provides a pharmaceutical composition comprising at least one bacterial strain selected from the genuses of *Akkermansia, Bacteroides, Clostridiales, Ruminoccoccus*, and *Faecalibacterium* and at least one pharmaceutically acceptable excipient.

In yet another aspect, the present disclosure provides a food supplement comprising at least one bacterial strain selected from the genuses of *Akkermansia, Bacteroides, Clostridiales, Ruminoccoccus*, and *Faecalibacterium.*

In yet another aspect, the present disclosure provides a pharmaceutical composition comprising at least one bacterial strain selected from the genuses of *Akkermansia, Bacteroides, Clostridiales, Ruminoccoccus*, and *Faecalibacterium*, a compound of formula I, and at least one pharmaceutically acceptable excipient.

In yet another aspect, the present disclosure provides a food supplement comprising at least one bacterial strain selected from the genuses of *Akkermansia, Bacteroides, Clostridiales, Ruminoccoccus*, and *Faecalibacterium* and a compound of formula I.

In yet another aspect, the present disclosure provides method of treating obesity and/or food addiction with the compounds, compositions, and food supplements of the present disclosure.

BRIEF DESCRIPTION OF THE DRAWINGS

FIG. 8B depicts the IntPS/TrPS to Pu differences between subjects with and without FA.

FIG. 8B depicts the Brain Stem to PU differences between subjects with and without FA.

DETAILED DESCRIPTION OF THE INVENTION

Figure 1A:
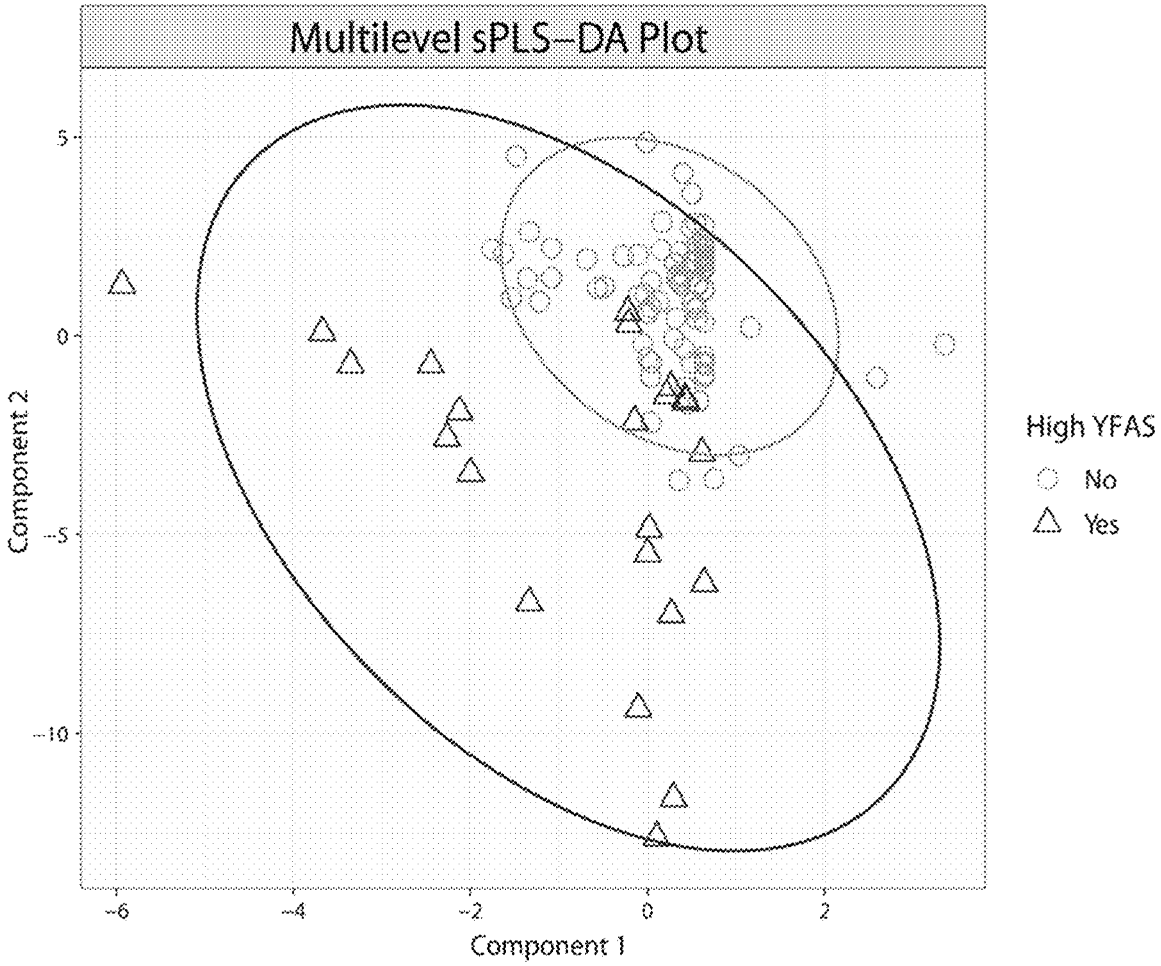
FIG. 1A shows a partial least square discriminant analysis of gut microbiome composition between patients with food addiction versus those without along with their 95% confidence ellipses.
Figure 1B:
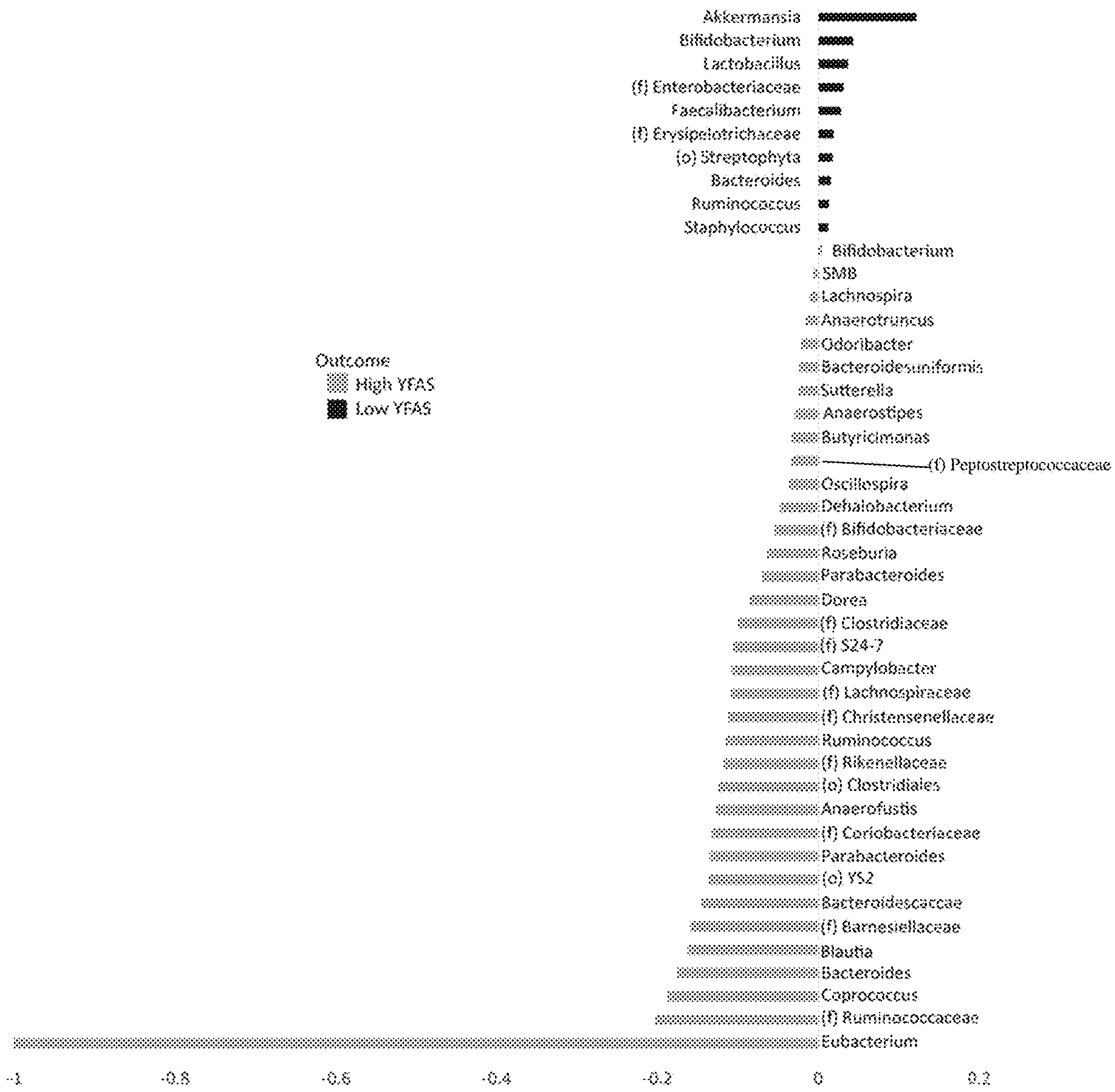
FIG. 1B shows a contribution plot indicating genera contributing to sPLS-DA plot that discriminate between the two groups of FIG. 1A.
Figure 2A:
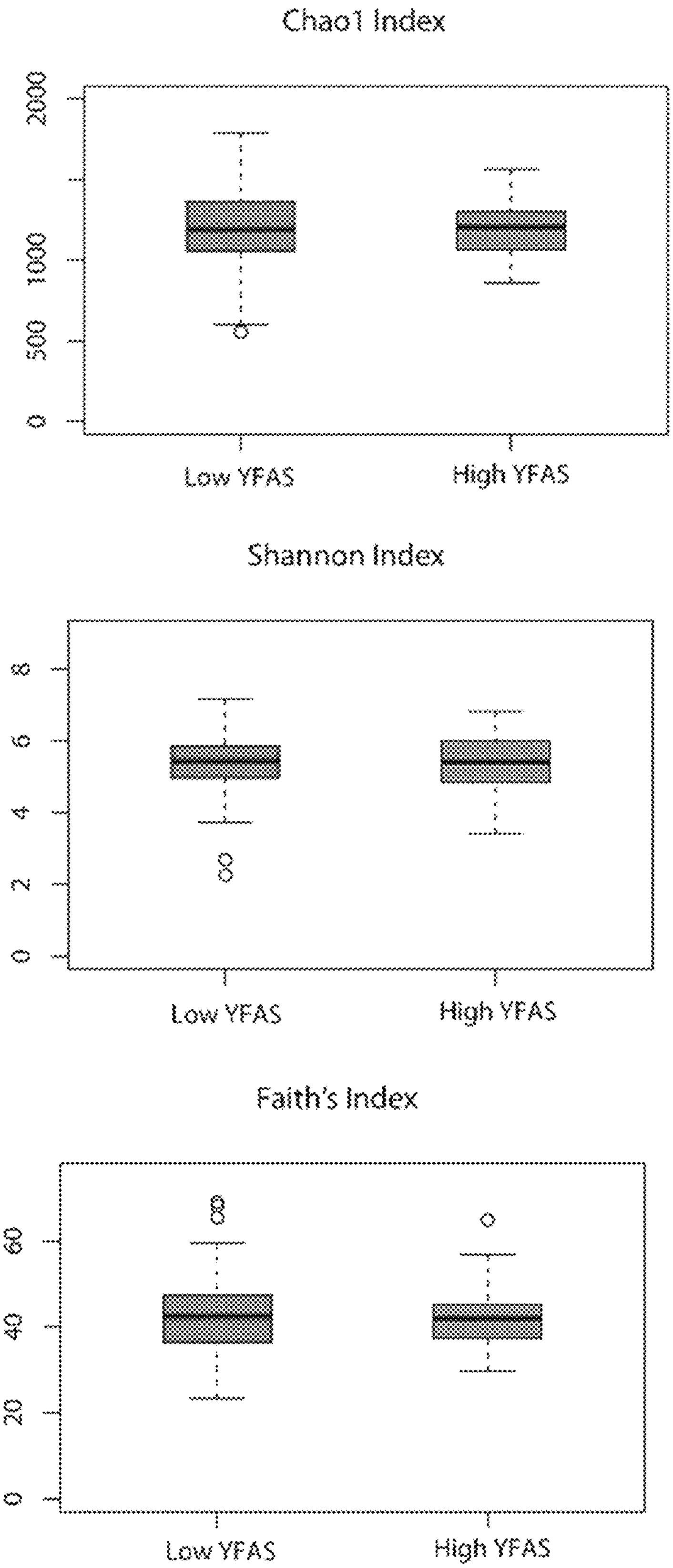
FIG. 2A shows Alpha diversity metrics (Chao1, Shannon, and Faith's Index) between patients high with a high YFAS vs. those with a low YFAS.
Figure 2B:
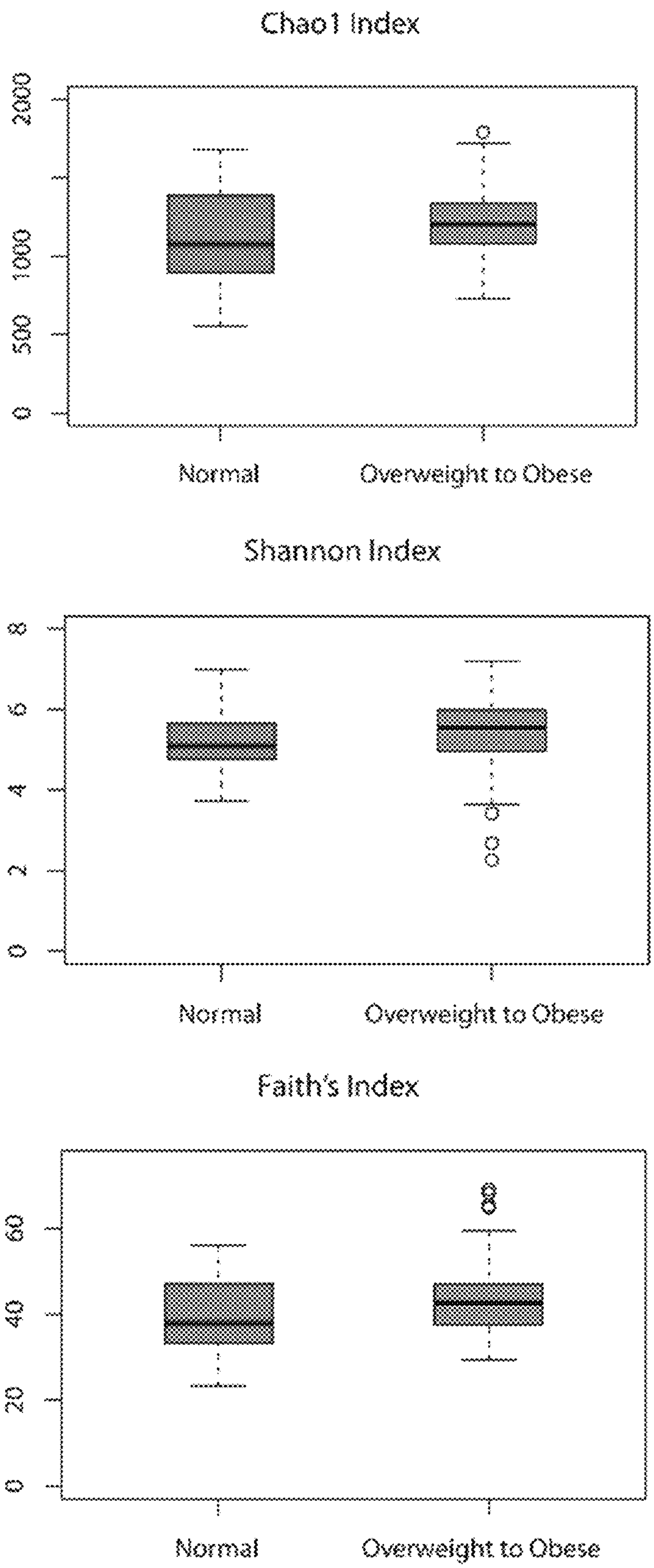
FIG. 2B shows Alpha diversity metrics (Chao1, Shannon, and Faith's Index) between patients high with a high BMI vs. those with a low BMI.
Figure 3A:
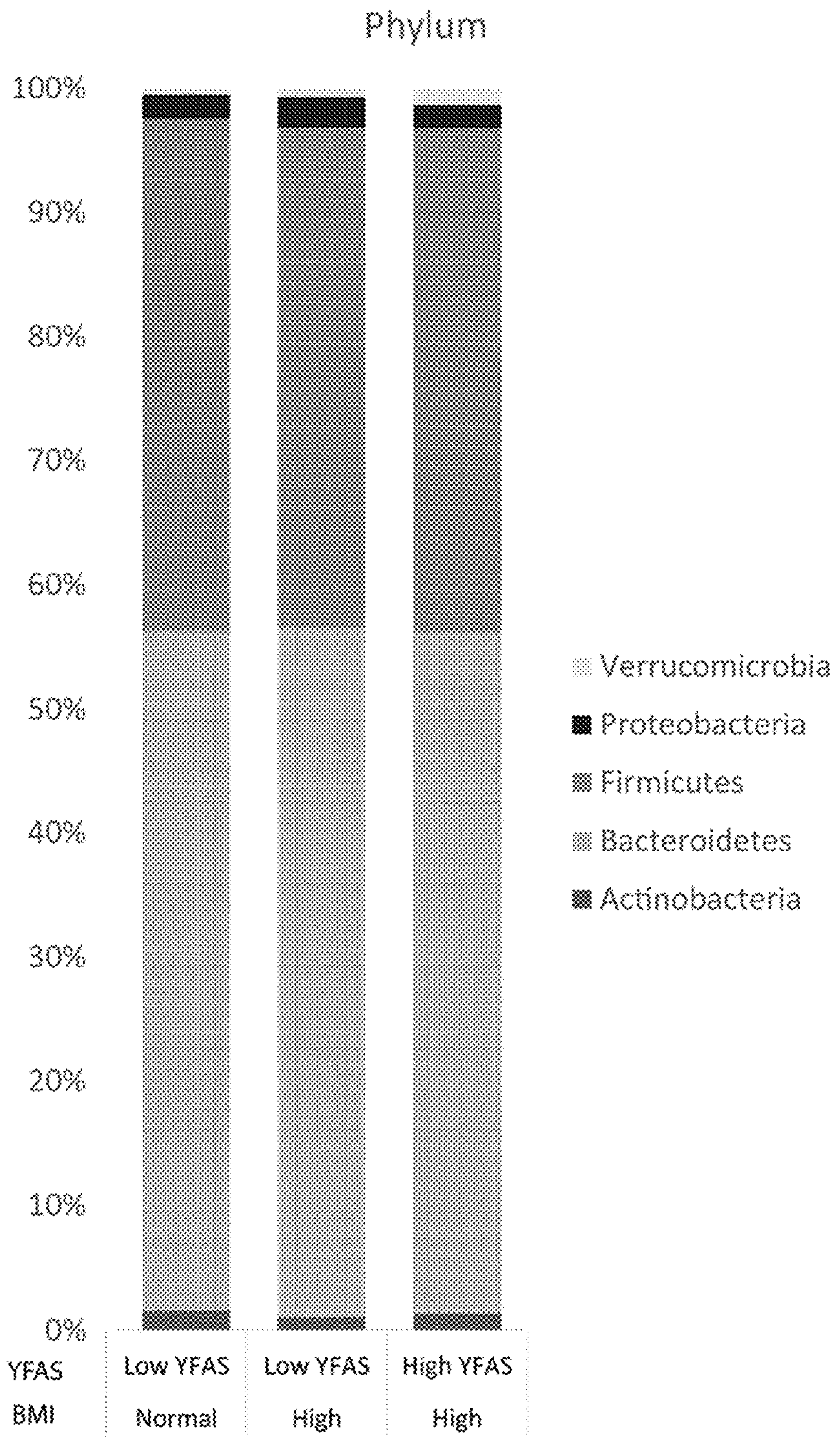
FIG. 3A shows a phylum taxonomic gut bacteria profile of subjects with a high YFAS vs. those with a low YFAS score.
Figure 3B:
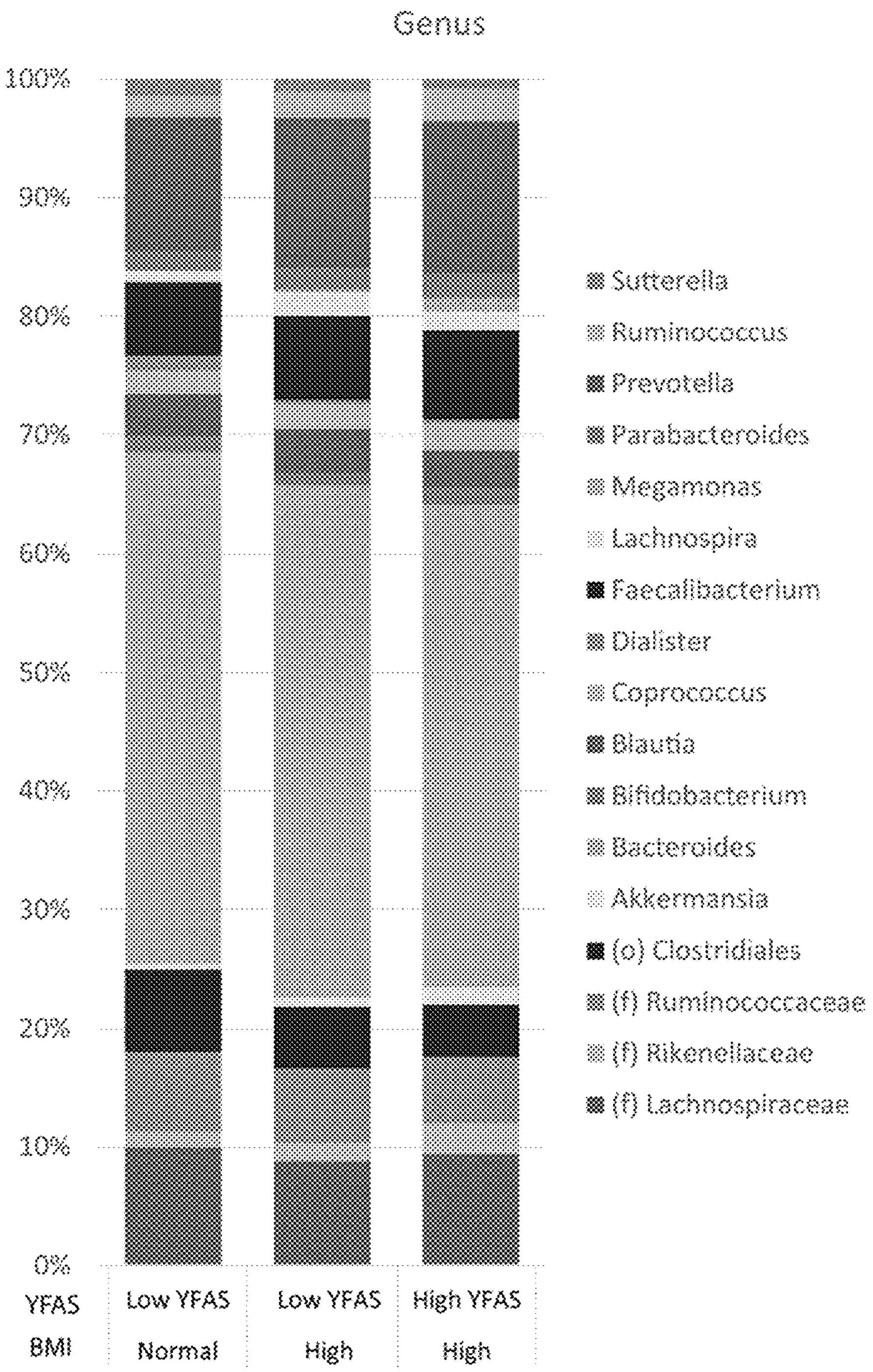
FIG. 3B shows a genus taxonomic gut bacteria profile of subjects with a high YFAS vs. those with a low YFAS score.
Figure 3C:
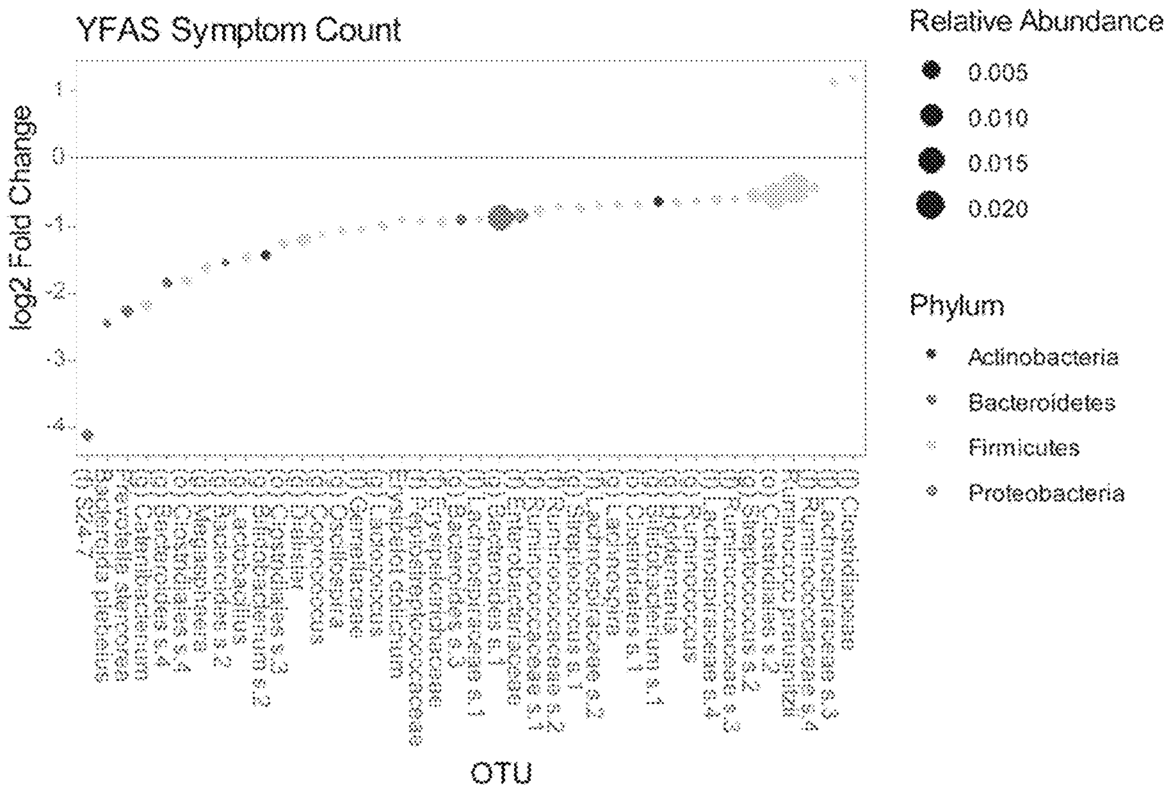
FIG. 3C depicts a DESEq2 analysis showing the OTUs that were correlated to YFAS score.
Figure 4:
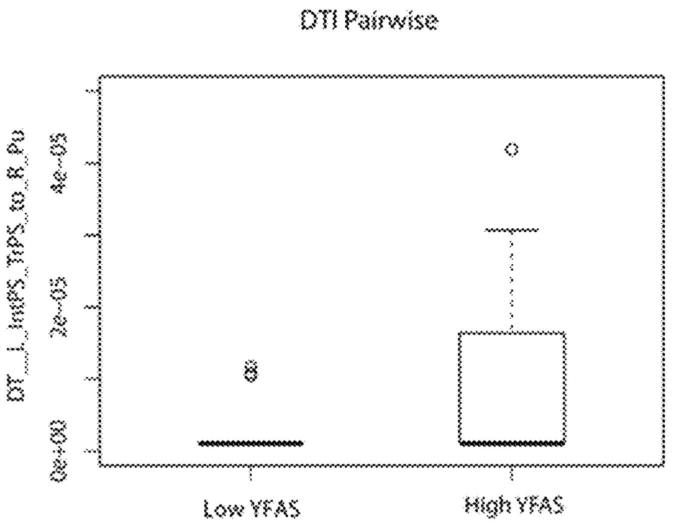
FIG. 4 shows the communication between the intraparietal sulcus/transverse parietal sulcus to the putamen of subjects with a low YFAS score vs. those with a high YFAS score.
Figure 5A:
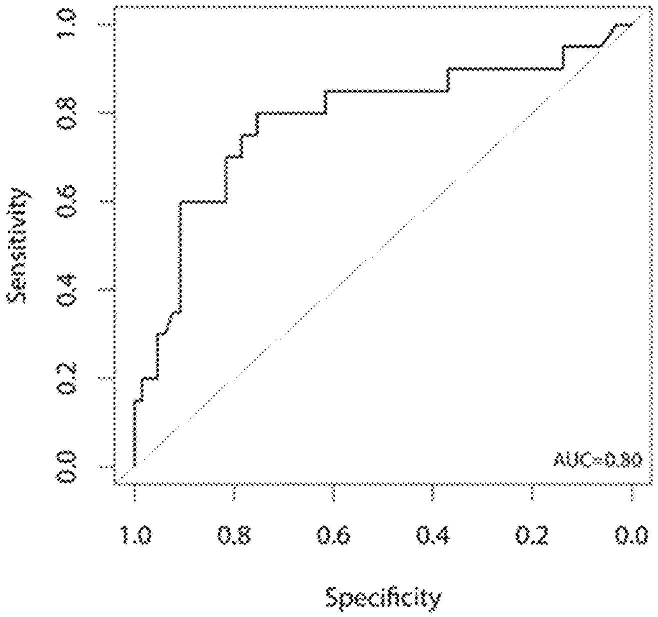
FIG. 5A shows a receiver operator curve for the random forest classifier at identifying patients with food addiction.
Figure 5B:
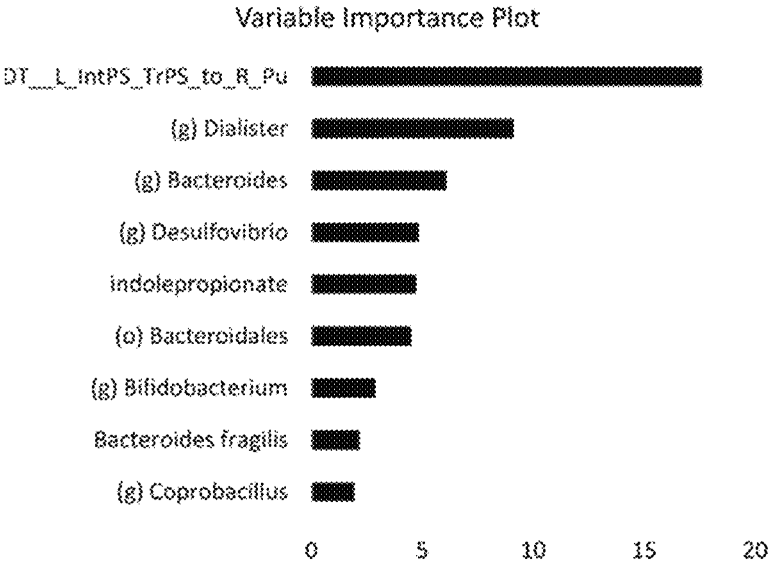
FIG. 5B shows a variable importance plot of the factors most important in the random forest classifier at predicting food addiction.

Food addiction (FA) is a primary driver of obesity. Overeating and sedentary lifestyles result in a positive energy imbalance, leading to adipose tissue accumulation. According to the Diagnostic and Statistical Manual of Mental Disorders (DSM-IV), an obsessive relationship with food fulfills behavioral criteria for diagnosis of substance addiction: 1) taking the substance in larger amounts than was intended; 2) inability to control its use; 3) taking the substance for a longer period of time than was intended; and 4) continued use despite adverse consequences. The Yale Food Addiction Scale (YFAS) has been developed and validated as a psychometrically sound measure to operationalize human cases of FA using the DSM-IV. YFAS scores were shown to be correlated with neural activation in brain areas contributing to cravings and reduced inhibitory control. Obesity profoundly impacts responsiveness of the brain reward system, altering the brain regions such as the striatum, prefrontal cortical regions and amygdala—areas likewise altered in drug addiction.

The gut microbiome is gaining recognition as significant player in the etiology of many diseases as well as obesity physiology. Research has shown that deviation from a core, lean gut microbiome profile is reflective of obesity. In addition to reduced bacterial diversity, there is alteration in bacterial gene representation and phylum-level modifications. Turnbaugh et al. found that obese profiles had less Bacteroidetes and more Actinobacteria, which represented 75% of obesity-enriched genes. There was 0% Bacteroidetes obese-enriched genes whereas Bacteroidetes made up 42% of the lean-enriched genes, where Actinobacteria were absent. Obesity-associated gut microbiomes also change pathways of food metabolism. Correlations between obesity pathophysiology and the gut microbiome have been observed through metagenomic and biochemical analyses, demonstrating that obese gut microbiomes absorb energy at higher efficiencies than lean gut microbiomes. This superfluous harvesting of energy results in accumulation of body fat. Demonstrated herein is the role of gut microbiome and fecal metabolite in relation to food addiction, as well as to addiction centers of the brain.

In one aspect, the present disclosure provides compounds of formula I:

I

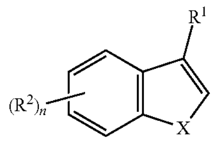

or a pharmaceutically acceptable salt thereof, wherein

X is O, $NR^3$, or S;

$R^1$ is alkyl, wherein the alkyl is optionally substituted, e.g., with hydroxyl, thio, sulfonamido, carbamate, carboxy, ester, or amido;

each $R^2$ is independently selected from alkyl, halo, hydroxyl, carboxyl, acyl, ester, thioester, alkoxy, phosphoryl, amino, amido, cyano, nitro, azido, alkylthio, alkenyl, alkynyl, cycloalkyl, heterocyclylalkyl, heteroaralkyl, sulfonamide, aryl, heteroaryl, heterocyclyl, and aralkyl;

$R^3$ is hydrogen or alkyl; and n is 0-4.

In certain embodiments of formula I, the compound is not

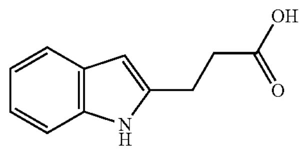 [SMILES: O=C(O)CCc1cc2ccccc2[nH]1]

or a salt thereof.

In certain embodiments of formula I, if $R^1$ is

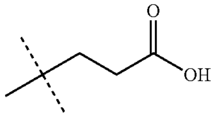

then n is 1-4. In certain embodiments of formula I, if $R^1$ is

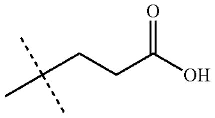

then X is O or S.

In certain preferred embodiments of formula I, $R^1$ is alkyl substituted with carboxy.

In other preferred embodiments of formula I, $R^1$ is alkyl substituted with hydroxyl, thio, sulfonamido, carbamate, ester, or amido.

In certain preferred embodiments of formula I, X is O or S.

In certain preferred embodiments of formula I, X is $NR^3$ and $R^3$ is alkyl, preferably lower alkyl.

In certain embodiments, n is 0. In certain preferred embodiments of formula I, n is 1-4.

In another aspect, the present disclosure provides a pharmaceutical composition comprising at least one bacterial strain selected from the genuses of *Akkermansia, Bacteroides, Clostridiales, Ruminoccoccus*, and *Faecalibacterium* and at least one pharmaceutically acceptable excipient. In certain embodiments, the bacterial strain is *Faecalibacterium prausnitzii*. In certain embodiments, the bacterial strain selected is selected from the genus of *Akkermansia*. In certain embodiments, the bacterial strain selected is selected from the genus of *Bacteroides*. In certain embodiments, the bacterial strain selected is selected from the genus of *Clostridiales*. In certain embodiments, the bacterial strain selected is selected from the genus of *Ruminoccoccus*. In certain embodiments, the bacterial strain selected is selected from the genus of *Faecalibacterium*.

In yet another aspect, the present disclosure provides a pharmaceutical composition comprising at least one bacterial strain selected from the genuses of *Bacteroides, Clostridiales, Ruminoccoccus*, and *Faecalibacterium*, a compound of formula I, and at least one pharmaceutically acceptable excipient. In some preferred embodiments, the compound is

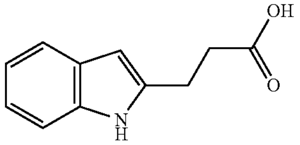 [SMILES: O=C(O)CCc1cc2ccccc2[nH]1]

or a salt thereof. In certain embodiments, the bacterial strain is *Faecalibacterium prausnitzii*. In certain embodiments, the bacterial strain selected is selected from the genus of *Akkermansia*. In certain embodiments, the bacterial strain selected is selected from the genus of *Bacteroides*. In certain embodiments, the bacterial strain selected is selected from the genus of *Clostridiales*. In certain embodiments, the bacterial strain selected is selected from the genus of *Ruminoccoccus*. In certain embodiments, the bacterial strain selected is selected from the genus of *Faecalibacterium*.

In yet another aspect, the present disclosure provides a food supplement comprising at least one bacterial strain selected from the genuses of *Akkermansia, Bacteroides, Clostridiales, Ruminoccoccus*, and *Faecalibacterium*. In certain embodiments, the bacterial strain is *Faecalibacterium prausnitzii*. In certain embodiments, the bacterial strain selected is selected from the genus of *Akkermansia*. In certain embodiments, the bacterial strain selected is selected from the genus of *Bacteroides*. In certain embodiments, the bacterial strain selected is selected from the genus of *Clostridiales*. In certain embodiments, the bacterial strain selected is selected from the genus of *Ruminoccoccus*. In certain embodiments, the bacterial strain selected is selected from the genus of *Faecalibacterium*.

In yet another aspect, the present disclosure provides a food supplement comprising at least one bacterial strain selected from the genuses of *Bacteroides, Clostridiales, Ruminoccoccus*, and *Faecalibacterium* and a compound of formula I. In some preferred embodiments, the compound is

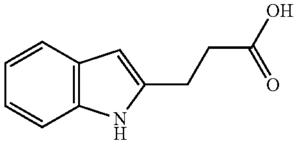 [SMILES: O=C(O)CCc1cc2ccccc2[nH]1]

or a salt thereof. In certain embodiments, the bacterial strain is *Faecalibacterium prausnitzii*. In certain embodiments, the bacterial strain selected is selected from the genus of *Akkermansia*. In certain embodiments, the bacterial strain selected is selected from the genus of *Bacteroides*. In certain embodiments, the bacterial strain selected is selected from the genus of *Clostridiales*. In certain embodiments, the bacterial strain selected is selected from the genus of *Ruminoccoccus*. In certain embodiments, the bacterial strain selected is selected from the genus of *Faecalibacterium*.

In yet another aspect, the present disclosure provides methods of treating obesity in a subject, comprising administering to a subject in need thereof a compound, composition, or food supplement of the disclosure. In certain embodiments, the subject has a reduced number of bacteria from a bacterial strain selected from the genuses of *Akkermansia, Bacteroides, Clostridiales, Ruminoccoccus*, and *Faecalibacterium* as compared to an individual with a healthy weight. In certain embodiments, the subject has a reduced number of bacteria from a bacterial strain selected from the genuses of *Bacteroides, Clostridiales, Ruminoccoccus*, and *Faecalibacterium*. In certain embodiments, the subject has an increased number of bacteria from a bacterial strain selected from the genus of *Megamonas* as compared to an individual with a healthy weight. In certain embodiments, the subject has reduced levels of indolepropionate as compared to an individual with a healthy weight.

In certain embodiments, the method further comprises:

(a) obtaining a biological sample from the subject; and (b) measuring in the biological sample an amount of at least one bacterial strain selected from the genuses of *Bacteroides, Clostridiales, Ruminoccoccus*, and *Faecalibacterium*.

In another aspect, the present disclosure provides methods of treating obesity in a subject comprising:

(a) obtaining a biological sample from the subject;

(b) measuring in the biological sample an amount of at least one bacterial strain selected from the genuses of *Akkermansia, Bacteroides, Clostridiales, Ruminococcus*, and *Faecalibacterium;*

(c) administering a compound, composition, or food supplement of the disclosure to the subject if the subject's levels of *Akkermansia, Bacteroides, Clostridiales, Ruminoccoccus*, or *Faecalibacterium* are reduced as compared to an individual with a healthy weight.

In another aspect, the present disclosure provides methods of treating obesity in a subject comprising:

(a) obtaining a biological sample from the subject;

(b) measuring in the biological sample an amount of at least one bacterial strain selected from the genuses of *Bacteroides, Clostridiales, Ruminoccoccus*, and *Faecalibacterium;*

(c) administering a compound, composition, or food supplement of the disclosure to the subject if the subject's levels of *Bacteroides, Clostridiales, Ruminoccoccus*, or *Faecalibacterium* are reduced as compared to an individual with a healthy weight.

In another aspect, the present disclosure provides methods of treating obesity in a subject comprising:

(a) obtaining a biological sample from the subject;

(b) measuring in the biological sample an amount of a bacterial strain selected from the genuses of *Megamonas;*

(c) administering a compound, composition, or food supplement of the disclosure to the subject if the subject's levels of *Megamonas* are increased as compared to an individual with a healthy weight.

In another aspect, the present disclosure provides methods of treating obesity in a subject comprising:

(a) obtaining a biological sample from the subject;

(b) measuring in the biological sample an amount of indolepropionate;

(c) administering a compound, composition, or food supplement of the disclosure to the subject if the subject's levels of indolepropionate are reduced as compared to an individual with a healthy weight.

In another aspect, the present disclosure provides methods of treating obesity in a subject comprising:

obtaining a first biological sample from the subject;

obtaining a second biological sample from the subject;

measuring in the first biological sample an amount of indolepropionate;

measuring in the second biological sample an amount of at least one bacterial strain selected from the genuses of *Akkermansia, Bacteroides, Clostridiales, Ruminococcus*, and *Faecalibacterium;* administering a compound, composition, or food supplement of the disclosure to the subject if:

the subject's levels of indolepropionate are reduced as compared to an individual with a healthy weight; and the subject's levels of *Akkermansia, Bacteroides, Clostridiales, Ruminoccoccus*, or *Faecalibacterium* are reduced as compared to an individual with a healthy weight.

In another aspect, the present disclosure provides methods of treating obesity in a subject comprising:

obtaining a first biological sample from the subject;

obtaining a second biological sample from the subject;

measuring in the first biological sample an amount of a bacterial strain selected from the genuses of *Megamonas;* measuring in the second biological sample an amount of at least one bacterial strain selected from the genuses of *Akkermansia, Bacteroides, Clostridiales, Ruminococcus*, and *Faecalibacterium;* administering a compound, composition, or food supplement of the disclosure to the subject if:

the subject's levels of *Akkermansia, Bacteroides, Clostridiales, Ruminoccoccus*, or *Faecalibacterium* are reduced as compared to an individual with a healthy weight; and the subject's levels of *Megamonas* are increased as compared to an individual with a healthy weight.

In another aspect, the present disclosure provides methods of treating obesity in a subject comprising:

obtaining a first biological sample from the subject;

obtaining a second biological sample from the subject;

measuring in the first biological sample an amount of indolepropionate;

measuring in the second biological sample an amount of a bacterial strain selected from the genuses of *Megamonas;* administering a compound, composition, or food supplement of the disclosure to the subject if:

the subject's levels of indolepropionate are reduced as compared to an individual with a healthy weight; and the subject's levels of *Megamonas* are increased as compared to an individual with a healthy weight.

In another aspect, the present disclosure provides methods of treating obesity in a subject comprising:

obtaining a first biological sample from the subject;

obtaining a second biological sample from the subject;

measuring in the first biological sample an amount of indolepropionate;

measuring in the second biological sample an amount of at least one bacterial strain selected from the genuses of *Akkermansia, Bacteroides, Clostridiales, Ruminococcus*, and *Faecalibacterium;* measuring in the second biological sample an amount of at least one bacterial strain selected from the genus of *Megamonas;* administering a compound, composition, or food supplement of the disclosure to the subject if:

the subject's levels of indolepropionate are reduced as compared to an individual with a healthy weight;

the subject's levels of *Akkermansia, Bacteroides, Clostridiales, Ruminoccoccus*, or *Faecalibacterium* are reduced as compared to an individual with a healthy weight; and the subject's levels of *Megamonas* are increased as compared to an individual with a healthy weight.

In another aspect, the present disclosure provides methods of treating obesity in a subject comprising:

obtaining a first biological sample from the subject;

obtaining a second biological sample from the subject;

obtaining a third biological sample from the subject;

measuring in the first biological sample an amount of indolepropionate;

measuring in the second biological sample an amount of at least one bacterial strain selected from the genuses of *Akkermansia, Bacteroides, Clostridiales, Ruminococcus*, and *Faecalibacterium;* measuring in the third biological sample an amount of a bacterial strain selected from the genus of *Megamonas;* administering a compound, composition, or food supplement of the disclosure to the subject if:

the subject's levels of indolepropionate are reduced as compared to an individual with a healthy weight;

the subject's levels of *Akkermansia, Bacteroides, Clostridiales, Ruminoccoccus*, or *Faecalibacterium* are reduced as compared to an individual with a healthy weight; and the subject's levels of *Megamonas* are increased as compared to an individual with a healthy weight.

In certain embodiments of the aforementioned methods, the subject has an increased connectivity between the intraparietal sulcus, transverse parietal sulcus, or brain stem and the putamen. In certain embodiments, the subject has an increased connectivity between the intraparietal sulcus and the putamen. In certain embodiments, the subject has an increased connectivity between the transverse parietal sulcus and the putamen. In certain embodiments, the subject has an increased connectivity between the brain stem and the putamen. In certain embodiments, the subjects increased connectivity between the intraparietal sulcus, transverse parietal sulcus, or brain stem and the putamen is determined by MRI (e.g., by Diffusion Tensor Imaging (DTI)). In certain preferred embodiments, the subjects increased connectivity between the intraparietal sulcus, transverse parietal sulcus, or brain stem and the putamen is determined by DTI. In certain preferred embodiments, the compound, composition, or food supplement of the disclosure is only administered if the subject has an increased connectivity between the intraparietal sulcus, transverse parietal sulcus, or brain stem and the putamen.

In certain embodiments of the aforementioned methods, the subject is suffering from food addiction.

In certain embodiments of the aforementioned methods, the subject has an excess of actinobacteria as compared to an individual with a healthy weight.

In certain preferred embodiments of the aforementioned methods, the subject is female.

In certain preferred embodiments of the aforementioned methods, the subject is of African American or Hispanic descent.

In certain embodiments of the aforementioned methods, the subject has a YFAS score greater than 3.

In certain embodiments of the aforementioned methods, the Chao1 Index, Faith Index, or Shannon Index of the subject is higher as compared to a subject of a BMI between 18.5-25.

In certain embodiments of the aforementioned methods, the method also treats food addiction.

In certain embodiments of the aforementioned methods, the bacterial strain is *Akkermansia*. In certain embodiments, the bacterial strain is *Bacteroides*. In certain embodiments, the bacterial strain is *Clostridiales*. In certain embodiments, the bacterial strain is *Faecalibacterium*. In certain embodiments, the bacterial strain is *Ruminococcocus*.

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); subcutaneously; transdermally (for example as a patch applied to the skin); and topically (for example, as a cream, ointment or spray applied to the skin). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in microencapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans; and other mammals such as equines, cattle, swine, sheep, cats, and dogs; poultry; and pets in general.

In certain embodiments, compounds of the invention may be used alone or conjointly administered with another type of therapeutic agent.

The present disclosure includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts. In certain embodiments, contemplated salts of the invention include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, 1-ascorbic acid, 1-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d-glucoheptonic acid, d-gluconic acid, d-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, 1-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, 1-pyroglutamic acid, salicylic acid, sebacic acid, stearic acid, succinic acid, sulfuric acid, 1-tartaric acid, thiocyanic acid, p-toluenesulfonic acid, trifluoroacetic acid, and undecylenic acid acid salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Bacterial Compositions

In certain aspects, provided herein are bacterial compositions comprising a strain selected from the genuses of *Bacteroides, Clostridiales, Ruminoccoccus*, and *Faecalibacterium*. In some embodiments, the bacterial formulation comprises a bacterium and/or a combination of bacteria described herein and a pharmaceutically acceptable carrier.

In certain embodiments, at least 50%, 55%, 60%, 65%, 70%, 75%, 80%, 85%, 90%, 91%, 92%, 93%, 94%, 95%, 96%, 97%, 98% or 99% of the bacteria in the bacterial composition are selected from the genuses of *Bacteroides, Clostridiales, Ruminoccoccus*, and *Faecalibacterium*, or a combination thereof. In certain embodiments, substantially all of the bacteria in the bacterial composition are selected from the genuses of *Bacteroides, Clostridiales, Ruminoccoccus*, and *Faecalibacterium*, or a combination thereof. In certain embodiments, the bacterial composition comprises at least $1\times10^3$ colony forming units (CFUs), $1\times10^4$ colony forming units (CFUs), $1\times10^5$ colony forming units (CFUs), $5\times10^5$ colony forming units (CFUs), $1\times10^6$ colony forming units (CFUs), $2\times10^6$ colony forming units (CFUs), $3\times10^6$ colony forming units (CFUs), $4\times10^6$ colony forming units (CFUs), $5\times10^6$ colony forming units (CFUs), $6\times10^6$ colony forming units (CFUs), $7\times10^6$ colony forming units (CFUs), $8\times10^6$ colony forming units (CFUs), $9\times10^6$ colony forming units (CFUs), $1\times10^7$ colony forming units (CFUs), $2\times10^7$ colony forming units (CFUs), $3\times10^7$ colony forming units (CFUs), $4\times10^7$ colony forming units (CFUs), $5\times10^7$ colony forming units (CFUs), $6\times10^7$ colony forming units (CFUs), $7\times10^7$ colony forming units (CFUs), $8\times10^7$ colony forming units (CFUs), $9\times10^7$ colony forming units (CFUs), $1\times10^8$ colony forming units (CFUs), $2\times10^8$ colony forming units (CFUs), $3\times10^8$ colony forming units (CFUs), $4\times10^8$ colony forming units (CFUs), $5\times10^8$ colony forming units (CFUs), $6\times10^8$ colony forming units (CFUs), $7\times10^8$ colony forming units (CFUs), $8\times10^8$ colony forming units (CFUs), $9\times10^8$ colony forming units (CFUs), $1\times10^9$ colony forming units (CFUs), $5\times10^9$ colony forming units (CFUs), $1\times10^{10}$ colony forming units (CFUs) $5\times10^{10}$ colony forming units (CFUs), $1\times10^{11}$ colony forming units (CFUs) $5\times10^{11}$ colony forming units (CFUs), $1\times10^{12}$ colony forming units (CFUs) $5\times10^{12}$ colony forming units (CFUs), $1\times10^{13}$ colony forming units (CFUs) of selected from the genuses of *Bacteroides, Clostridiales, Ruminoccoccus*, and *Faecalibacterium*, or a combination thereof.

The selected dosage level will depend upon a variety of factors including the subject's diet, the route of administration, the time of administration, the residence time of the particular microorganism being employed, the duration of the treatment, other drugs, compounds and/or materials used in combination with the particular composition employed, the age, sex, weight, condition, general health and prior medical history of the patient being treated, and like factors well known in the medical arts.

A physician or veterinarian having ordinary skill in the art can readily determine and prescribe the effective amount of the bacterial composition required. For example, the physician or veterinarian could prescribe and/or administer doses of the bacteria employed in the v composition at levels lower than that required in order to achieve the desired therapeutic effect and gradually increase the dosage until the desired effect is achieved.

In some embodiments, probiotic formulations containing bacteria selected from the genuses of *Bacteroides, Clostridiales, Ruminoccoccus*, and *Faecalibacterium*, or a combination thereofs are provided as encapsulated, enteric coated, or powder forms, with doses ranging up to $10^{11}$ cfu (e.g., up to $10^{10}$ cfu). In some embodiments, the composition comprises $5\times10^{11}$ cfu of bacteria selected from the genuses of *Bacteroides, Clostridiales, Ruminoccoccus*, and *Faecalibacterium*, or a combination thereof and 10% (w/w) corn starch in a capsule. In some embodiments, the capsule is enteric coated, e.g., for duodenal release at pH 5.5. In some embodiments, the composition comprises a powder of freeze-dried bacteria selected from the genuses of *Bacteroides, Clostridiales, Ruminoccoccus*, and *Faecalibacterium*, or a combination thereof which is deemed to have "Qualified Presumption of Safety" (QPS) status. In some embodiments, the composition is storage-stable at frozen or refrigerated temperature. As used herein, "stably stored" or "storage-stable" refer to a composition in which cells are able to withstand storage for extended periods of time (e.g., at least one month, or two, three, four, six, or twelve months or more) with a less than 95%, 90%, 80%, 70%, 60%, 50%, 40%, 30%, 20%, 15%, 10%, 5%, or 1% decrease in cell viability.

Methods for producing microbial compositions may include three main processing steps. The steps are: organism banking, organism production, and preservation. In certain embodiments, a sample that contains an abundance bacteria selected from the genuses of *Bacteroides, Clostridiales, Ruminoccoccus*, and *Faecalibacterium*, or a combination thereof may be cultured by avoiding an isolation step.

For banking, bacteria selected from the genuses of *Bacteroides, Clostridiales, Ruminoccoccus*, and *Faecalibacterium*, or a combination thereof included in the microbial composition may be (1) isolated directly from a specimen or taken from a banked stock, (2) optionally cultured on a nutrient agar or broth that supports growth to generate viable biomass, and (3) the biomass optionally preserved in multiple aliquots in long-term storage.

In embodiments using a culturing step, the agar or broth may contain nutrients that provide essential elements and specific factors that enable growth. An example would be a medium composed of 20 g/L glucose, 10 g/L yeast extract, 10 g/L soy peptone, 2 g/L citric acid, 1.5 g/L sodium phosphate monobasic, 100 mg/L ferric ammonium citrate, 80 mg/L magnesium sulfate, 10 mg/L hemin chloride, 2 mg/L calcium chloride, 1 mg/L menadione. Another example would be a medium composed of 10 g/L beef extract, 10 g/L peptone, 5 g/L sodium chloride, 5 g/L dextrose, 3 g/L yeast extract, 3 g/L sodium acetate, 1 g/L soluble starch, and 0.5 g/L L-cysteine HCl, at pH 6.8. A variety of microbiological media and variations are well known in the art (e.g., R. M. Atlas, Handbook of Microbiological Media (2010) CRC Press). Culture media can be added to the culture at the start, may be added during the culture, or may be intermittently/continuously flowed through the culture. The strains in the bacterial composition may be cultivated alone, as a subset of the microbial composition, or as an entire collection comprising the microbial composition. As an example, a first strain may be cultivated together with a second strain in a mixed continuous culture, at a dilution rate lower than the maximum growth rate of either cell to prevent the culture from washing out of the cultivation.

The inoculated culture is incubated under favorable conditions for a time sufficient to build biomass. For microbial compositions for human use this is often at 37° C. temperature, pH, and other parameter with values similar to the normal human niche. The environment may be actively controlled, passively controlled (e.g., via buffers), or allowed to drift. For example, for anaerobic bacterial compositions, an anoxic/reducing environment may be employed. This can be accomplished by addition of reducing agents such as cysteine to the broth, and/or stripping it of oxygen. As an example, a culture of a bacterial composition may be grown at 37° C., pH 7, in the medium above, pre-reduced with 1 g/L cysteine-HCl.

When the culture has generated sufficient biomass, it may be preserved for banking. The organisms may be placed into a chemical milieu that protects from freezing (adding 'cryoprotectants'), drying ('lyoprotectants'), and/or osmotic shock ('osmoprotectants'), dispensing into multiple (optionally identical) containers to create a uniform bank, and then treating the culture for preservation. Containers are generally impermeable and have closures that assure isolation from the environment. Cryopreservation treatment is accomplished by freezing a liquid at ultra-low temperatures (e.g., at or below −80° C.). Dried preservation removes water from the culture by evaporation (in the case of spray drying or 'cool drying') or by sublimation (e.g., for freeze drying, spray freeze drying). Removal of water improves long-term microbial composition storage stability at temperatures elevated above cryogenic conditions. Microbial composition banking may be done by culturing and preserving the strains individually, or by mixing the strains together to create a combined bank. As an example of cryopreservation, a microbial composition culture may be harvested by centrifugation to pellet the cells from the culture medium, the supernatant decanted and replaced with fresh culture broth containing 15% glycerol. The culture can then be aliquoted into 1 mL cryotubes, sealed, and placed at −80° C. for long-term viability retention. This procedure achieves acceptable viability upon recovery from frozen storage.

Microbial production may be conducted using similar culture steps to banking, including medium composition and culture conditions described above. It may be conducted at larger scales of operation, especially for clinical development or commercial production. At larger scales, there may be several subcultivations of the microbial composition prior to the final cultivation. At the end of cultivation, the culture is harvested to enable further formulation into a dosage form for administration. This can involve concentration, removal of undesirable medium components, and/or introduction into a chemical milieu that preserves the microbial composition and renders it acceptable for administration via the chosen route. For example, a microbial composition may be cultivated to a concentration of $10^{10}$ CFU/mL, then concentrated 20-fold by tangential flow microfiltration; the spent medium may be exchanged by diafiltering with a preservative medium consisting of 2% gelatin, 100 mM trehalose, and 10 mM sodium phosphate buffer. The suspension can then be freeze-dried to a powder and titrated.

After drying, the powder may be blended to an appropriate potency, and mixed with other cultures and/or a filler such as microcrystalline cellulose for consistency and ease of handling, and the bacterial composition formulated as provided herein.

In certain aspects, provided are bacterial compositions for administration in subjects. In some embodiments, the bacterial compositions are combined with additional active and/or inactive materials in order to produce a final product, which may be in single dosage unit or in a multi-dose format.

In some embodiments, the composition comprises at least one carbohydrate. A "carbohydrate" refers to a sugar or polymer of sugars. The terms "saccharide," "polysaccharide," "carbohydrate," and "oligosaccharide" may be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate may be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose wherein a hydroxyl group is removed, 2'-fluororibose wherein a hydroxyl group is replaced with a fluorine, or N-acetylglucosamine, a nitrogen-containing form of glucose (e.g., 2'-fluororibose, deoxyribose, and hexose). Carbohydrates may exist in many different forms, for example, conformers, cyclic forms, acyclic forms, stereoisomers, tautomers, anomers, and isomers.

In some embodiments, the composition comprises at least one lipid. As used herein, a "lipid" includes fats, oils, triglycerides, cholesterol, phospholipids, fatty acids in any form including free fatty acids. Fats, oils and fatty acids can be saturated, unsaturated (cis or trans) or partially unsaturated (cis or trans). In some embodiments the lipid comprises at least one fatty acid selected from lauric acid (12:0), myristic acid (14:0), palmitic acid (16:0), palmitoleic acid (16:1), margaric acid (17:0), heptadecenoic acid (17:1), stearic acid (18:0), oleic acid (18:1), linoleic acid (18:2), linolenic acid (18:3), octadecatetraenoic acid (18:4), arachidic acid (20:0), eicosenoic acid (20:1), eicosadienoic acid (20:2), eicosatetraenoic acid (20:4), eicosapentaenoic acid (20:5) (EPA), docosanoic acid (22:0), docosenoic acid (22:1), docosapentaenoic acid (22:5), docosahexaenoic acid (22:6) (DHA), and tetracosanoic acid (24:0). In some embodiments the composition comprises at least one modified lipid, for example a lipid that has been modified by cooking.

In some embodiments, the composition comprises at least one supplemental mineral or mineral source. Examples of minerals include, without limitation: chloride, sodium, calcium, iron, chromium, copper, iodine, zinc, magnesium, manganese, molybdenum, phosphorus, potassium, and selenium. Suitable forms of any of the foregoing minerals include soluble mineral salts, slightly soluble mineral salts, insoluble mineral salts, chelated minerals, mineral complexes, non-reactive minerals such as carbonyl minerals, and reduced minerals, and combinations thereof.

In some embodiments, the composition comprises at least one supplemental vitamin. The at least one vitamin can be fat-soluble or water soluble vitamins. Suitable vitamins include but are not limited to vitamin C, vitamin A, vitamin E, vitamin B12, vitamin K, riboflavin, niacin, vitamin D, vitamin B6, folic acid, pyridoxine, thiamine, pantothenic acid, and biotin. Suitable forms of any of the foregoing are salts of the vitamin, derivatives of the vitamin, compounds having the same or similar activity of the vitamin, and metabolites of the vitamin.

In some embodiments, the composition comprises an excipient. Non-limiting examples of suitable excipients include a buffering agent, a preservative, a stabilizer, a binder, a compaction agent, a lubricant, a dispersion enhancer, a disintegration agent, a flavoring agent, a sweetener, and a coloring agent.

In some embodiments, the excipient is a buffering agent. Non-limiting examples of suitable buffering agents include sodium citrate, magnesium carbonate, magnesium bicarbonate, calcium carbonate, and calcium bicarbonate.

In some embodiments, the excipient comprises a preservative. Non-limiting examples of suitable preservatives include antioxidants, such as alpha-tocopherol and ascorbate, and antimicrobials, such as parabens, chlorobutanol, and phenol.

In some embodiments, the composition comprises a binder as an excipient. Non-limiting examples of suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, and combinations thereof.

In some embodiments, the composition comprises a lubricant as an excipient. Non-limiting examples of suitable lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

In some embodiments, the composition comprises a dispersion enhancer as an excipient. Non-limiting examples of suitable dispersants include starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

In some embodiments, the compositions of the present invention are combined with a carrier (e.g., a pharmaceutically acceptable carrier) which is physiologically compatible with the gastrointestinal tissue of the subject(s) to which it is administered. Carriers can be comprised of solid-based, dry materials for formulation into tablet, capsule or powdered form; or the carrier can be comprised of liquid or gel-based materials for formulations into liquid or gel forms. The specific type of carrier, as well as the final formulation depends, in part, upon the selected route(s) of administration. The therapeutic composition of the present invention may also include a variety of carriers and/or binders. In some embodiments, the carrier is micro-crystalline cellulose (MCC) added in an amount sufficient to complete the one gram dosage total weight. Carriers can be solid-based dry materials for formulations in tablet, capsule or powdered form, and can be liquid or gel-based materials for formulations in liquid or gel forms, which forms depend, in part, upon the routes of administration. Typical carriers for dry formulations include, but are not limited to: trehalose, malto-dextrin, rice flour, microcrystalline cellulose (MCC) magnesium sterate, inositol, FOS, GOS, dextrose, sucrose, and like carriers. Suitable liquid or gel-based carriers include but are not limited to: water and physiological salt solutions; urea; alcohols and derivatives (e.g., methanol, ethanol, propanol, butanol); glycols (e.g., ethylene glycol, propylene glycol, and the like). Preferably, water-based carriers possess a neutral pH value (i.e., approximately pH 7.0). Other carriers or agents for administering the compositions described herein are known in the art, e.g., in U.S. Pat. No. 6,461,607.

In some embodiments, the composition comprises a disintegrant as an excipient. In some embodiments the disintegrant is a non-effervescent disintegrant. Non-limiting examples of suitable non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pectin, and tragacanth. In some embodiments the disintegrant is an effervescent disintegrant. Non-limiting examples of suitable effervescent disintegrants include sodium bicarbonate in combination with citric acid, and sodium bicarbonate in combination with tartaric acid.

In some embodiments, the bacterial formulation comprises an enteric coating or micro encapsulation. In certain embodiments, the enteric coating or micro encapsulation improves targeting to a desired region of the gastrointestinal tract. For example, in certain embodiments, the bacterial composition comprises an enteric coating and/or microcapsules that dissolves at a pH associated with a particular region of the gastrointestinal tract. In some embodiments, the enteric coating and/or microcapsules dissolve at a pH of about 5.5-6.2 to release in the duodenum, at a pH value of about 7.2-7.5 to release in the ileum, and/or at a pH value of about 5.6-6.2 to release in the colon. Exemplary enteric coatings and microcapsules are described, for example, in U.S. Pat. Pub. No. 2016/0022592, which is hereby incorporated by reference in its entirety.

In some embodiments, the composition is a food product (e.g., a food or beverage) such as a health food or beverage, a food or beverage for infants, a food or beverage for pregnant women, athletes, senior citizens or other specified group, a functional food, a beverage, a food or beverage for specified health use, a dietary supplement, a food or beverage for patients, or an animal feed. Specific examples of the foods and beverages include various beverages such as juices, refreshing beverages, tea beverages, drink preparations, jelly beverages, and functional beverages; alcoholic beverages such as beers; carbohydrate-containing foods such as rice food products, noodles, breads, and pastas; paste products such as fish hams, sausages, paste products of seafood; retort pouch products such as curries, food dressed with a thick starchy sauces, and Chinese soups; soups; dairy products such as milk, dairy beverages, ice creams, cheeses, and yogurts; fermented products such as fermented soybean pastes, yogurts, fermented beverages, and pickles; bean products; various confectionery products, including biscuits, cookies, and the like, candies, chewing gums, gummies, cold desserts including jellies, cream caramels, and frozen desserts; instant foods such as instant soups and instant soy-bean soups; microwavable foods; and the like. Further, the examples also include health foods and beverages prepared in the forms of powders, granules, tablets, capsules, liquids, pastes, and jellies. The composition may be a fermented food product, such as, but not limited to, a fermented milk product. Non-limiting examples of fermented food products include kombucha, sauerkraut, pickles, miso, tempeh, natto, kimchi, raw cheese, and yogurt. The composition may also be a food additive, such as, but not limited to, an acidulent (e.g., vinegar). Food additives can be divided into several groups based on their effects. Non-limiting examples of food additives include acidulents (e.g., vinegar, citric acid, tartaric acid, malic acid, fumaric acid, and lactic acid), acidity regulators, anticaking agents, antifoaming agents, foaming agents, antioxidants (e.g., vitamin C), bulking agents (e.g., starch), food coloring, fortifying agents, color retention agents, emulsifiers, flavors and flavor enhancers (e.g., monosodium glutamate), flour treatment agents, glazing agents, humectants, tracer gas, preservatives, stabilizers, sweeteners, and thickeners.

In certain embodiments, the bacteria disclosed herein are administered in conjunction with a prebiotic to the subject. Prebiotics are carbohydrates which are generally indigestible by a host animal and are selectively fermented or metabolized by bacteria. Prebiotics may be short-chain carbohydrates (e.g., oligosaccharides) and/or simple sugars (e.g., mono- and disaccharides) and/or mucins (heavily glycosylated proteins) that alter the composition or metabolism of a microbiome in the host. The short chain carbohydrates are also referred to as oligosaccharides, and usually contain from 2 or 3 and up to 8, 9, 10, 15 or more sugar moieties. When prebiotics are introduced to a host, the prebiotics affect the bacteria within the host and do not directly affect the host. In certain aspects, a prebiotic composition can selectively stimulate the growth and/or activity of one of a limited number of bacteria in a host. Prebiotics include oligosaccharides such as fructooligosaccharides (FOS) (including inulin), galactooligosaccharides (GOS), trans-galactooligosaccharides, xylooligosaccharides (XOS), chitooligosaccharides (COS), soy oligosaccharides (e.g., stachyose and raffinose) gentiooligosaccharides, isomaltooligosaccharides, mannooligosaccharides, maltooligosaccharides and mannanoligosaccharides. Oligosaccharides are not necessarily single components, and can be mixtures containing oligosaccharides with different degrees of oligomerization, sometimes including the parent disaccharide and the monomeric sugars. Various types of oligosaccharides are found as natural components in many common foods, including fruits, vegetables, milk, and honey. Specific examples of oligosaccharides are lactulose, lactosucrose, palatinose, glycosyl sucrose, guar gum, gum Arabic, tagalose, amylose, amylopectin, pectin, xylan, and cyclodextrins. Prebiotics may also be purified or chemically or enzymatically synthesized.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, Mass. (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, C.A. (1985).

All of the above, and any other publications, patents and published patent applications referred to in this application are specifically incorporated by reference herein. In case of conflict, the present specification, including its specific definitions, will control.

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents whose structure is known, and those whose structure is not known. The ability of such agents to inhibit AR or promote AR degradation may render them suitable as "therapeutic agents" in the methods and compositions of this disclosure.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

A "therapeutically effective amount" or a "therapeutically effective dose" of a drug or agent is an amount of a drug or an agent that, when administered to a subject will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, and the nature and extent of the condition being treated, such as cancer or MDS. The skilled worker can readily determine the effective amount for a given situation by routine experimentation.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the compounds of the present invention can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term "optionally substituted" refers to the replacement of one to six hydrogen radicals in a given structure with the radical of a specified substituent including, but not limited to: hydroxyl, hydroxyalkyl, alkoxy, halogen, alkyl, nitro, silyl, acyl, acyloxy, aryl, cycloalkyl, heterocyclyl, amino, aminoalkyl, cyano, haloalkyl, haloalkoxy, $—OCO—CH_2—O$-alkyl, $—OP(O)(O\text{-alkyl})_2$ or $—CH_2—OP(O)(O\text{-alkyl})_2$. Preferably, "optionally substituted" refers to the replacement of one to four hydrogen radicals in a given structure with the substituents mentioned above. More preferably, one to three hydrogen radicals are replaced by the substituents as mentioned above. It is understood that the substituent can be further substituted.

As used herein, the term "alkyl" refers to saturated aliphatic groups, including but not limited to $C_1$-$C_{10}$ straight-chain alkyl groups or $C_1$-$C_{10}$ branched-chain alkyl groups. Preferably, the "alkyl" group refers to $C_1$-$C_6$ straight-chain alkyl groups or $C_1$-$C_6$ branched-chain alkyl groups. Most preferably, the "alkyl" group refers to $C_1$-$C_4$ straight-chain alkyl groups or $C_1$-$C_4$ branched-chain alkyl groups. Examples of "alkyl" include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. The "alkyl" group may be optionally substituted.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_{1-30}$ for straight chains, $C_{3-30}$ for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "$C_{x-y}$" or "$C_x$-$C_y$", when used in conjunction with a chemical moiety, such as, acyl, acyloxy, alkyl, alkenyl, alkynyl, or alkoxy is meant to include groups that contain from x to y carbons in the chain. $C_0$alkyl indicates a hydrogen where the group is in a terminal position, a bond if internal. A $C_{1-6}$alkyl group, for example, contains from one to six carbon atoms in the chain.

The term "alkylamino", as used herein, refers to an amino group substituted with at least one alkyl group.

The term "alkylthio", as used herein, refers to a thiol group substituted with an alkyl group and may be represented by the general formula alkylS-.

The term "amide", as used herein, refers to a group

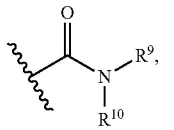

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

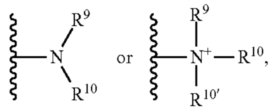

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

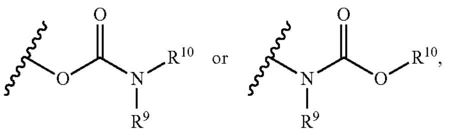

wherein $R^9$ and $R^{10}$ independently represent hydrogen or a hydrocarbyl group.

The term "carbocyclylalkyl", as used herein, refers to an alkyl group substituted with a carbocycle group.

The term “carbocycle” includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term “fused carbocycle” refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary “carbocycles” include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. “Carbocycles” may be substituted at any one or more positions capable of bearing a hydrogen atom.

The term “carbocyclylalkyl”, as used herein, refers to an alkyl group substituted with a carbocycle group.

The term “carbonate” is art-recognized and refers to a group $—OCO_2—$.

The term “carboxy”, as used herein, refers to a group represented by the formula $—CO_2H$.

The term “ester”, as used herein, refers to a group $—C(O)OR^9$ wherein $R^9$ represents a hydrocarbyl group.

The term “ether”, as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include “alkoxyalkyl” groups, which may be represented by the general formula alkyl-O-alkyl.

The terms “halo” and “halogen” as used herein means halogen and includes chloro, fluoro, bromo, and iodo.

The terms “hetaralkyl” and “heteroaralkyl”, as used herein, refers to an alkyl group substituted with a hetaryl group.

The terms “heteroaryl” and “hetaryl” include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms “heteroaryl” and “hetaryl” also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term “heteroatom” as used herein means an atom of any element other than carbon or hydrogen. Preferred heteroatoms are nitrogen, oxygen, and sulfur.

The term “heterocyclylalkyl”, as used herein, refers to an alkyl group substituted with a heterocycle group.

The terms “heterocyclyl”, “heterocycle”, and “heterocyclic” refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms “heterocyclyl” and “heterocyclic” also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term “hydrocarbyl”, as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term “hydroxyalkyl”, as used herein, refers to an alkyl group substituted with a hydroxy group.

The term “lower” when used in conjunction with a chemical moiety, such as, acyl, acyloxy, alkyl, alkenyl, alkynyl, or alkoxy is meant to include groups where there are ten or fewer atoms in the substituent, preferably six or fewer. A “lower alkyl”, for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms “polycyclyl”, “polycycle”, and “polycyclic” refer to two or more rings (e.g., cycloalkyls, cycloalkenyls, cycloalkynyls, aryls, heteroaryls, and/or heterocyclyl s) in which two or more atoms are common to two adjoining rings, e.g., the rings are “fused rings”. Each of the rings of the polycycle can be substituted or unsubstituted. In certain embodiments, each ring of the polycycle contains from 3 to 10 atoms in the ring, preferably from 5 to 7.

The term “sulfate” is art-recognized and refers to the group $—OSO_3H$, or a pharmaceutically acceptable salt thereof.

The term “sulfonamide” is art-recognized and refers to the group represented by the general formulae

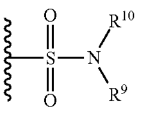

or

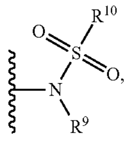

wherein $R^9$ and $R^{10}$ independently represents hydrogen or hydrocarbyl.

The term “sulfoxide” is art-recognized and refers to the group —S(O)—.

The term "sulfonate" is art-recognized and refers to the group $SO_3H$, or a pharmaceutically acceptable salt thereof.

The term "sulfone" is art-recognized and refers to the group $—S(O)_2—$.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioester", as used herein, refers to a group $—C(O)SR^9$ or $—SC(O)R^9$ wherein $R^9$ represents a hydrocarbyl.

The term "thioether", as used herein, is equivalent to an ether, wherein the oxygen is replaced with a sulfur.

The term "urea" is art-recognized and may be represented by the general formula

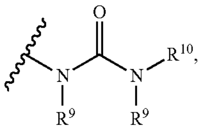

wherein $R^9$ and $R^{10}$ independently represent hydrogen or a hydrocarbyl.

The term "modulate" as used herein includes the inhibition or suppression of a function or activity (such as cell proliferation) as well as the enhancement of a function or activity.

"Pharmaceutically acceptable salt" or "salt" is used herein to refer to an acid addition salt or a basic addition salt which is suitable for or compatible with the treatment of patients.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixture and separate individual isomers.

Some of the compounds may also exist in tautomeric forms. Such forms, although not explicitly indicated in the formulae described herein, are intended to be included within the scope of the present disclosure.

"Prodrug" or "pharmaceutically acceptable prodrug" refers to a compound that is metabolized, for example hydrolyzed or oxidized, in the host after administration to form the compound of the present disclosure (e.g., compounds of formula I). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of Formula I. The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

As used herein the term "healthy weight" refers to an individual with a body mass index between 18.5 and 24.9.

EXAMPLES

The invention now being generally described, it will be more readily understood by reference to the following examples which are included merely for purposes of illustration of certain aspects and embodiments of the present invention, and are not intended to limit the invention.

Example 1: Exemplary Analysis of Individuals for Food Addiction

Methods

Subject Population

The prevalence of FA differs by sex, with females with obesity having a higher prevalence (15-30%) than males with obesity (~5%). Due to the higher prevalence of FA in females, the analysis was focused on female subjects. The sample was comprised of 105 right-handed female subjects, between the age of 18-50 years old without significant medical or psychiatric conditions. Medical and psychiatric conditions were screened using a standardized screening sheet and a physical exam by a trained registered nurse. Subjects were excluded for the following reasons: pregnant or lactating, substance use disorder, abdominal surgery, tobacco dependence (half a pack or more daily), extreme strenuous exercise (>8 h of continuous exercise per week), current or past psychiatric illness and major medical (including inflammatory bowel disease, active malignancy, organ failure, and diabetes) or neurological conditions (including Alzheimer's disease, Parkinson's disease, history of stroke, traumatic brain injury, or seizure disorder). Subjects taking medications that interfere with the central nervous system or regular use of analgesic drugs were excluded. Since female sex hormones such as estrogen are known to effect brain structure and function, we only included females who were premenopausal. Subjects with hypertension, diabetes, metabolic syndrome or eating disorders were excluded to minimize confounding effects. No subjects exceeded 400 lbs due to magnetic resonance imaging scanning weight limits. Subjects were also excluded if they had been on antibiotics or probiotics with 3 months of recruitment.

Multimodal magnetic resonance brain imaging (MM), anthropometrics (height, body weight, and waist-hip ratio measurements, body mass index), measures of appetite and FA, and stool samples for 16S ribosomal RNA gene sequencing and metabolomics were collected.

Food Addiction Questionnaire

FA was assessed using the Yale Food Addiction Scale (YFAS) questionnaire, a 25-item scale developed to assess food addiction by assessing signs of substance-dependence symptoms in eating behavior. This scale is based upon the substance dependence criteria as found in the DSM-4 (e.g., tolerance [marked increase in amount; marked decrease in effect], withdrawal [agitation, anxiety, physical symptoms], and loss of control [eating to the point of feeling physical ill]). The YFAS questionnaire is a 25-question survey that measures several aspects of FA behavior: food dependence, withdrawal, tolerance, continued use despite problems, time spent eating, loss of control, inability to cut down, and clinically significant impairment. Food addiction was defined as having a YFAS symptom count ≥3 with clinically significant impairment or distress. Clinically significant impairment or distress was defined as having a at least one positive response to the following two questions in the YFAS questionnaire: "My behavior with respect to food and eating causes significant distress" and "I experience significant problems in my ability to function effectively (daily routine, job/school, social activities, family activities, health difficulties) because of food and eating," similar to previously published works. The YFAS has displayed a good internal reliability (Kuder—Richardson $\alpha$=0.86).

Intestinal Microbial 16S rRNA Gene Sequencing

Fresh stool was collected within 1 month of the patient's brain MRI scan. All samples were stored at −80° C. before 16S rRNA sequencing. DNA was extracted from frozen fecal samples using the PowerSoil DNA Isolation Kit (MO BIO Laboratories, Carlsbad, Calif.) with bead beating following the manufacturers protocol. The V4 hypervariable region of the 16S rRNA gene was amplified using the 515F and 806R primers according to a published protocol. PCR products were purified by a commercial kit and sequenced on the Illumina HiSeq 2500 platform. In most microbial species, the V4 region is approximately 253 bp, and only deviates from this length by a few base pairs. Because the HiSeq 2500 rapid run mode enables paired 150-bp reads, the reads overlap to generate high-quality, full-length sequences of the entire region. The 806R primer includes a unique sequence tag to barcode the samples, enabling 200-400 specimens to be run as one batch with a targeted depth of 250,000 sequences/sample. The base pair reads were processed using QIIME v1.9.1 with default parameters. The taxonomic assignments of sequences will be performed using open reference operational taxonomic unit (OTU) picking in QIIME against the Greengenes database preclustered at 97% identity. OTUs were removed if they were present in less than 10% of samples.

Fecal Metabolomics

Fecal samples were aliquoted and shipped to Metabolon for processing and analysis as a single batch on their global metabolomics and bioinformatics platform. Data was curated by mass spectroscopy using established protocols and software as previously described. Because of our interest in the gut-brain axis, only tryptophan derived metabolites were examined.

Brain Magnetic Resonance Imaging

Multiple brain imaging modalities was used in this study:

Grey matter morphology: measures gray matter, white matter and cerebral spinal fluid; and Diffusion spectrum imaging (DSI): measures the microscopic properties of white-matter and fiber track connectivity.

Structural MRI

High resolution T1-weighted images were acquired: echo time/repetition time (TE/TR)=3.26 ms/2200 ms, field of view (F0V)=220×220 mm slice thickness=1 mm, 176 slices, 256×256 voxel matrices, and voxel size=0.86×0.86×1 mm.

Diffusion-Weighted MRI

Diffusion-weighted magnetic resonance imaging was acquired according to two comparable acquisition protocols, in either 61 or 64 noncolinear directions with b=1000 s $mm^{-2}$, with 8 or 1 b=0 s $mm^{-2}$ images respectively, TE/TR==88 ms/TR=9500 ms, and FOV=256 mm with an acquisition matrix of 128×128, and a slice thickness of 2 mm, resulting in DTI data with 2 mm isotropic resolution.

Quality Control of MRI Data

Preprocessing for quality control involved bias field correction, coregistration, motion correction, spatial normalization, tissue segmentation, Fourier transformation for frequency distribution, and specific quantitative checks for DTI images (apparent diffusion coefficient and fractional anisotropy [FA]). Structural images were included based on compliance with acquisition protocol, full brain coverage, minimal motion (Gibbs ringing), absence of flow/zipper, and minor atrophy/vascular degeneration. Functional images were included based on compliance with acquisition protocol, full brain coverage, motion estimate of <½ voxel size between adjacent time points, low standard deviation across time series for all voxels, ghosting in cerebrum, minimal physiological noise (>0.2 Hz in frequency spectrum), and few to no outlier voxels, mean intensity shifts, or K-space "spikes." Preprocessing for diffusion-weighted imaging included visually checking for artifacts and motion on the raw diffusion weighted and $b_0$ images, visual assessment of FA and mean diffusitivity (MD) map quality, as well checking for physiologically feasible FA and MD values (FA of 0-0.1 and MD of 3-4 μm2/ms in ventricles, and FA of 0.6-0.9 and MD of 0.6-0.9 μm2/ms in splenium of corpus callosum). Maximum relative motion thresholds for translation and rotation for each direction (x, y, and z) were set at 2 mm and 2°, respectively. No subjects presented with serious adverse imaging artifacts and no subjects exceeded motion thresholds.

T1-image segmentation and regional parcellation were conducted using FreeSurfer v. 5.3.0 following the nomenclature described in the Destrieux and Harvard-Oxford subcortical atlas. This parcellation results in the labeling of 165 regions, 74 bilateral cortical structures, 7 subcortical structures, the midbrain, and the cerebellum.

Regional parcellation and tractography results were combined to produce a weighted, undirected connectivity matrix. The final estimate of white matter connectivity between each of the brain regions was determined based on the number of fiber tracts intersecting each region. Weights of the connections were then expressed as the absolute fiber count divided by the individual volumes of the two interconnected regions.

Brain Regions of Interest

Based on previous research, regions of interest were restricted to core regions of the reward network (basal ganglia: caudate nucleus, globus *pallidum*, putamen, thalamus, nucleus accumbens (NAcc), amygdala, and brainstem [including the substantia nigra/SN and ventral tegmental area/VTA]), as these regions have been implicated in brain-gut axis alterations associated with obesity.

Statistical Analysis

Baseline demographic characteristics differences were compared using student's test for continuous variables and chi-squared test for categorical variables. Means are expressed with their respective standard deviation. Multilevel sparse partial least square linear discriminant analysis (sPLS-DA) was done to analyze microbiome data using the Mixomics package in R. sPLS-DA identifies OTUs that discriminated patients with low YFAS from those with high YFAS by simultaneously performing feature selection and modeling using lasso penalization. sPLS-DA operates using a supervised framework to find linear combinations of a limited set of variables, here OTUs, that predicts YFAS status, similar to prior published works. Microbial alpha diversity (i.e. diversity within a sample) were calculated in QIIME using OTU-level data rarefied to 34,222 sequences. The significance of differences in alpha diversity metrics—Faith's phylogenetic diversity (Faith's PD), Chao1, and Shannon index—was calculated by analysis of variance. Association of microbial genera with low or high YFAS were evaluated using DESeq2 in R, which employs an empirical Bayesian approach to shrink dispersion and fit non-rarified count data to a negative binomial model. P-values for differential abundance were converted to q-values to correct for multiple hypothesis testing (<0.05 for significance). Metabolomics data were normalized and then fitted to a gaussian model with the limma package in R. Brain imaging data was compared between individuals with low YFAS as compared to those with high YFAS using a generalized linear model in R and p-values adjusted using false discover rate for multiple comparisons.

Random Forest Classifier

A random forest classifier was created in R to identify patients with high YFAS using the randomForest package with 1001 trees and mtry=2. The number of trees were varied from 100 to 10,000 at intervals of 500, and 1000 trees were selected as the parameter as it minimized the out-of-bag estimate of error. An odd number was used to prevent theoretical ties that may occur from forest generation. Similarly, various mtry were selected and an mtry of 2 was used as it gave the highest area under the receiver operating curve (AUC). Features in the random forest classifier included OTUs that were significantly different by DESeq2 analysis and metabolites and brain imaging data that was statistically different in patients with high YFAS. The accuracy of the random forest classifier was estimated using a 5-fold cross-validation.

Results

Patient Characteristics

Through patient recruitment, 105 female patients were enrolled in the study. A high YFAS score was a score of ≥3. Twenty-three patients (21.9%) had a high YFAS. The average age was 32.4 years±10.2. There was no statistical difference by age in patients with high YFAS as compared to those with low YFAS. Patients with high YFAS tended to be more overweight or obese (p-value=0.01). Of the patients with high YFAS, 73.9% (17/23) of those patients were obese as compared to 41.4% (34/82) of patients with low YFAS. The average BMI in patients with high YFAS was 34.3±5.6 and the average BMI in patients with low YFAS was 29.2±5.6 (p-value=0.0001).

Gut Microbial Signature as it Relates to Food Addiction

Figure 6A:
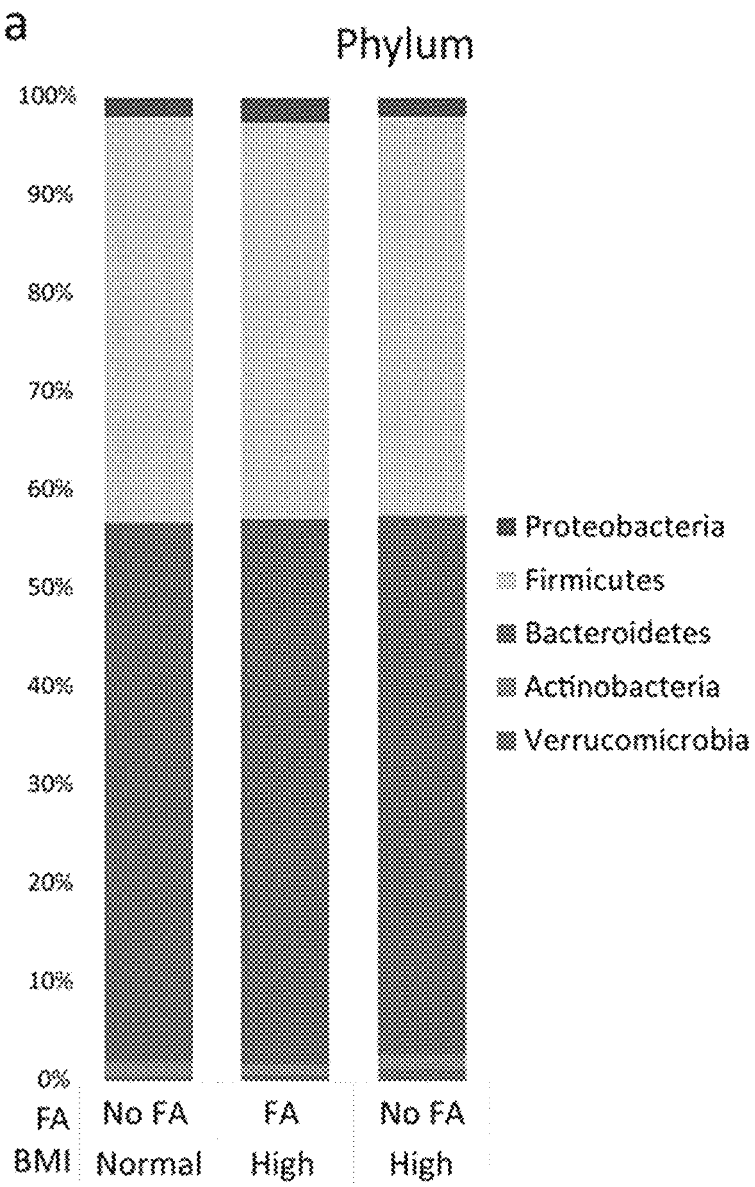
FIG. 6A shows taxonomic profiles between subjects with No Food Addiction (No FA) and Food Addiction (FA) on a phylum level. Only taxa ≥1% relative abundance are shown.
Figure 6B:
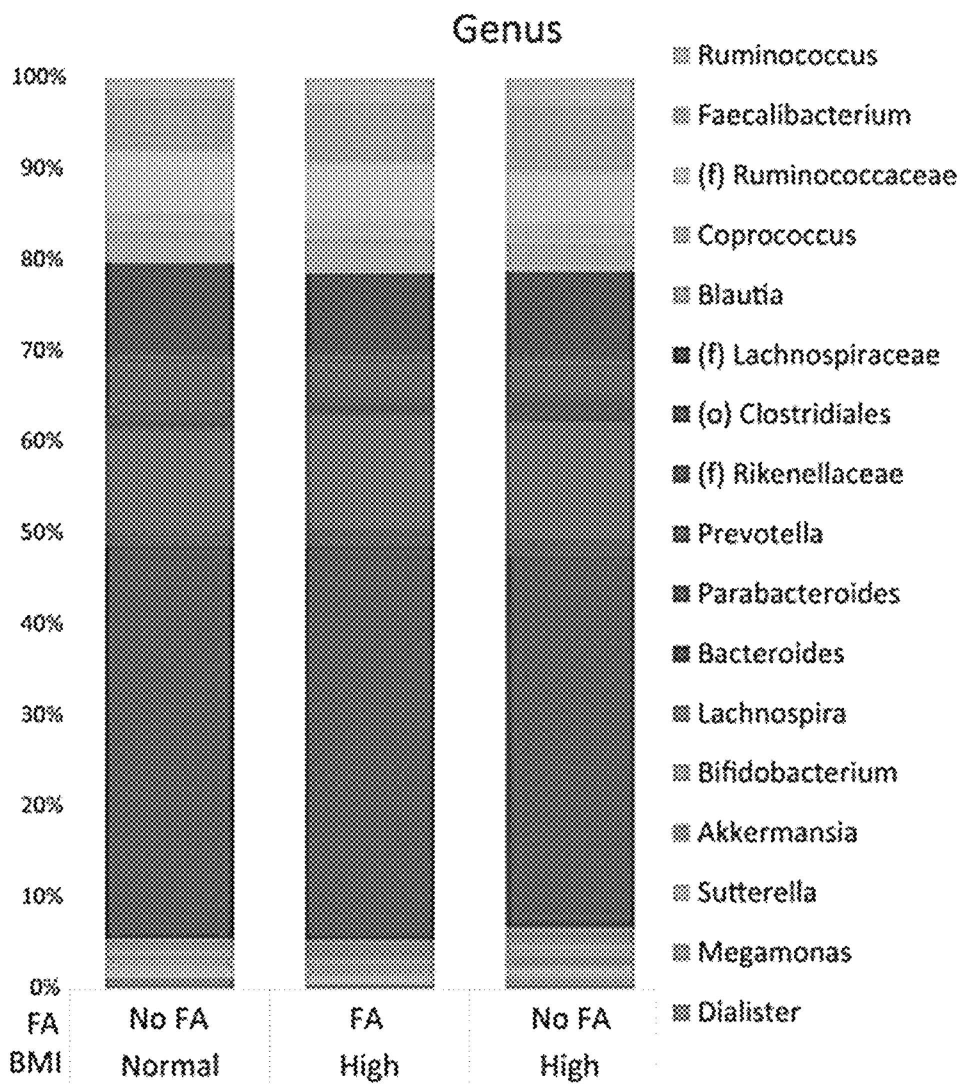
FIG. 6B shows taxonomic profiles between subjects with No Food Addiction (No FA) and Food Addiction (FA) on a genus level. Only taxa ≥1% relative abundance are shown.
Figure 6C:
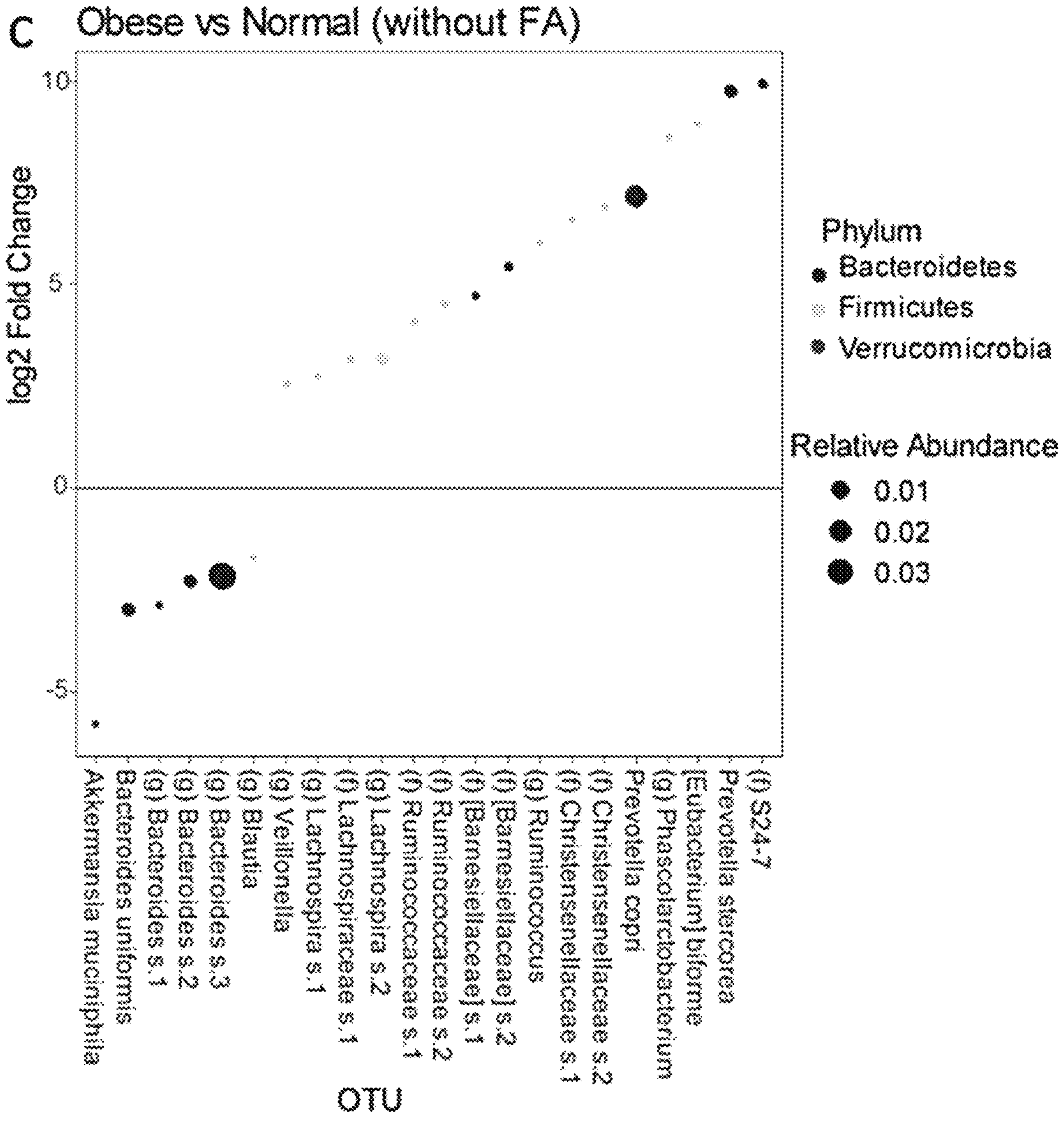
FIG. 6C shows the DESEq2 analysis of patients without FA comparing those with obesity and those with normal BMI showing several OTUs associated with obesity.
Figure 6D:
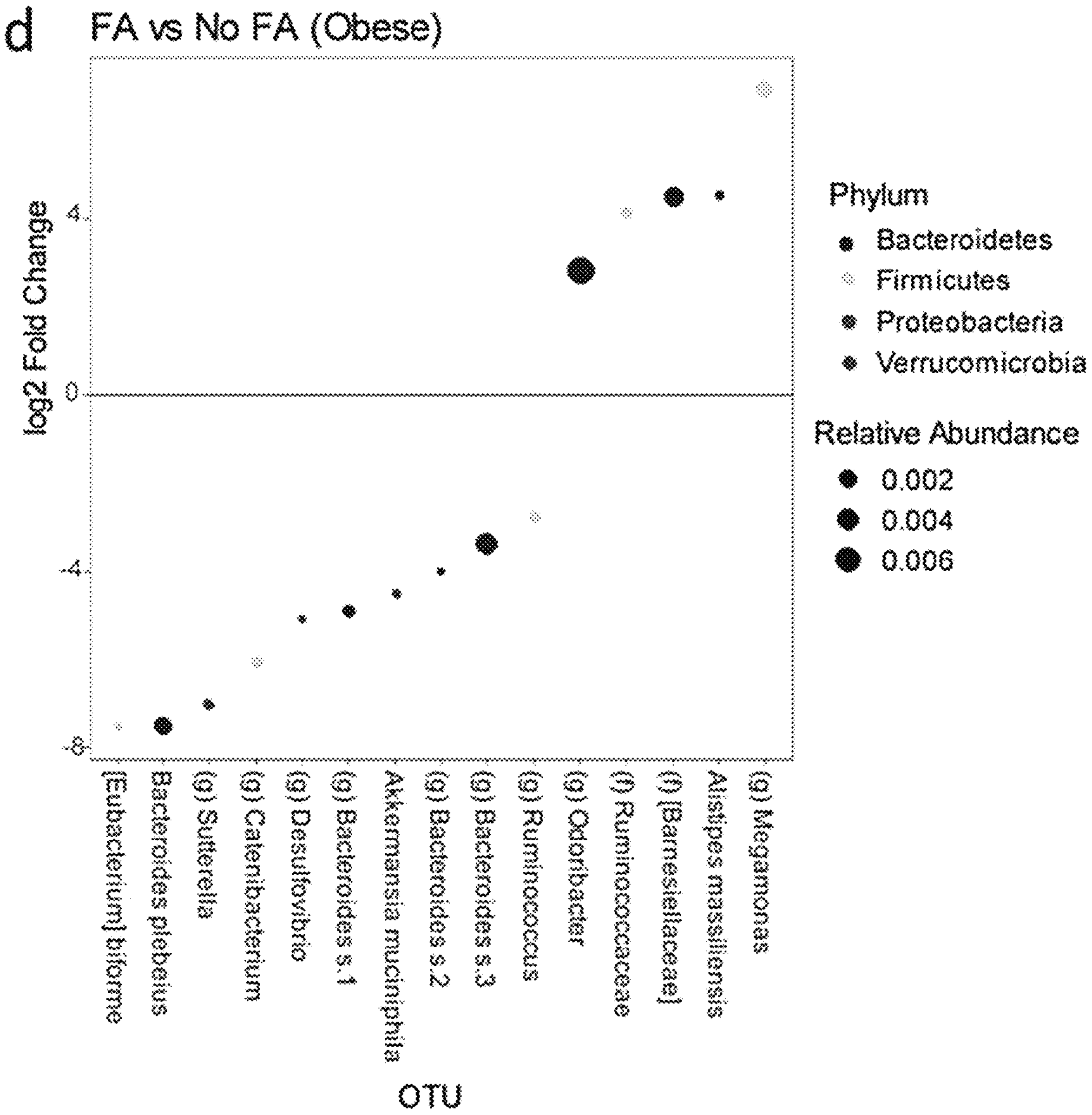
FIG. 6D shows the DESEq2 analysis of only patients with obesity showing several OTUs that are associated with FA.

There were no statistical differences in beta-diversity using Bray-Curtis dissimilarity between obese subjects with or without FA. There were also no statistical differences in any alpha diversity metrics between the microbial samples of obese subjects with FA as compared to those without FA. However, there was a significant difference in alpha diversity metrics by race/ethnicity with Caucasians and African-Americans having higher diversity than Hispanics. After adjusting for race/ethnicity there were no differences in subjects with a BMI of ≥25 to normal weight individuals by any alpha diversity metric. The taxonomic profiles of subjects with FA compared to subjects without FA on a phylum and genus level are summarized in FIGS. 6A & 6B, respectively. DESEq2 analysis of patients without FA identified 22 distinct OTUs that were associated with obesity as compared to normal weight individuals (FIG. 6C). Six OTUs were negatively correlated and 16 OTUs were positively correlated to obesity. The four highest abundant OTUs belong to the genera *Bacteroides*, and *Prevotella*. The OTU with the greatest negative fold change was *Akkermansia* muciniphila. DESEq2 analysis of patients with obesity identified 15 OTUs that were associated with FA (FIG. 6D). Ten OTUs were negatively associated with FA and 5 OTUs were positively associated with FA. The largest abundant OTU belonged to the genus *Bacteroides*, while the OTU with the largest positive fold change was *Megamonas* and the OTU with the largest negative fold change was *Eubacterium* biforme. Similarly to patients with obesity without FA as compared to normal weight patients, *Akkermansia* muciniphila was negatively associated with FA in patients with obesity.

Figure 7A:
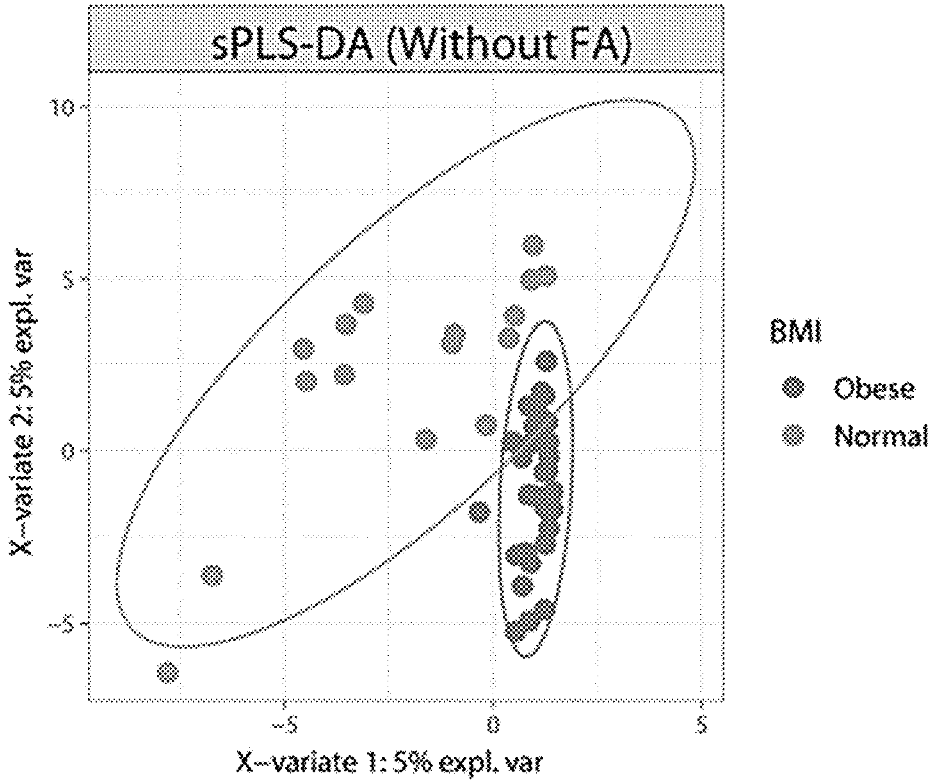
FIG. 7A is a plot of the partial least square discriminant analysis of the gut microbiome composition between subjects with obesity without food addiction versus those with normal BMI and without FA along with their 95% confidence ellipses.
Figure 7B:
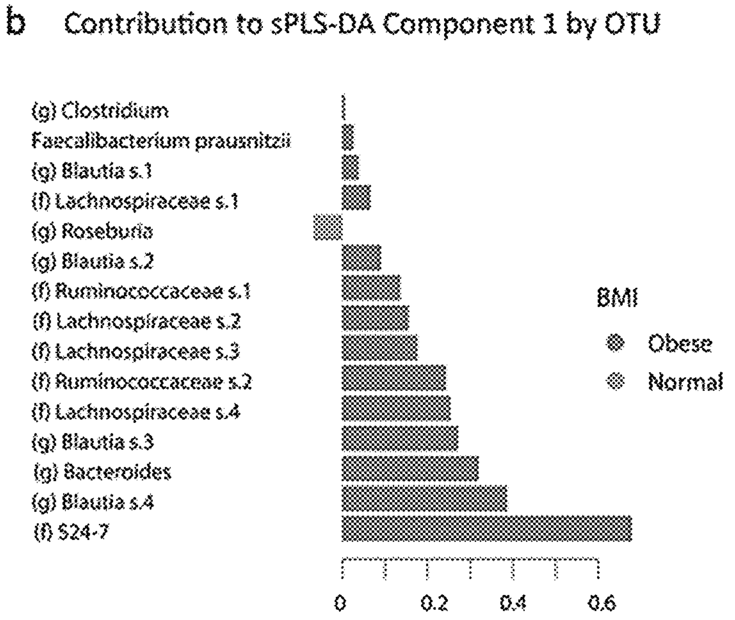
FIG. 7B shows contributing OTUs to the plot depicted in FIG. 7A.
Figure 7C:
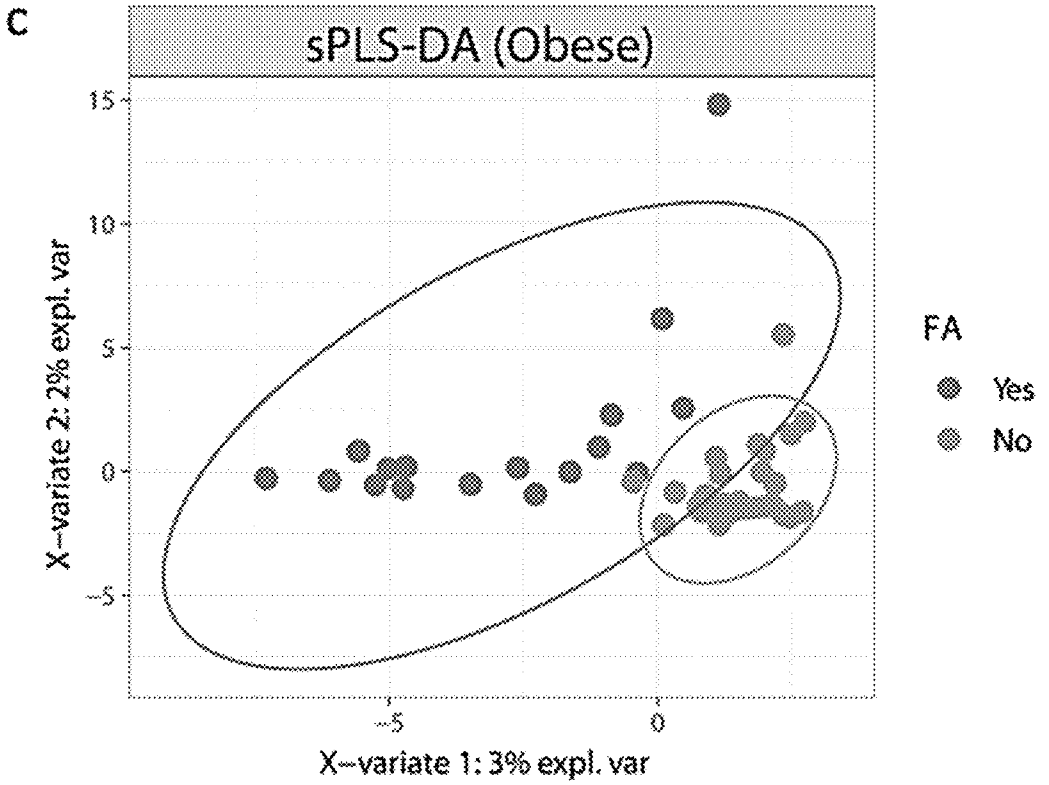
FIG. 7C is a plot of the partial least square discriminant analysis of the gut microbiome composition between obese subjects with food addiction versus those without FA along with their 95% confidence ellipses.
Figure 7D:
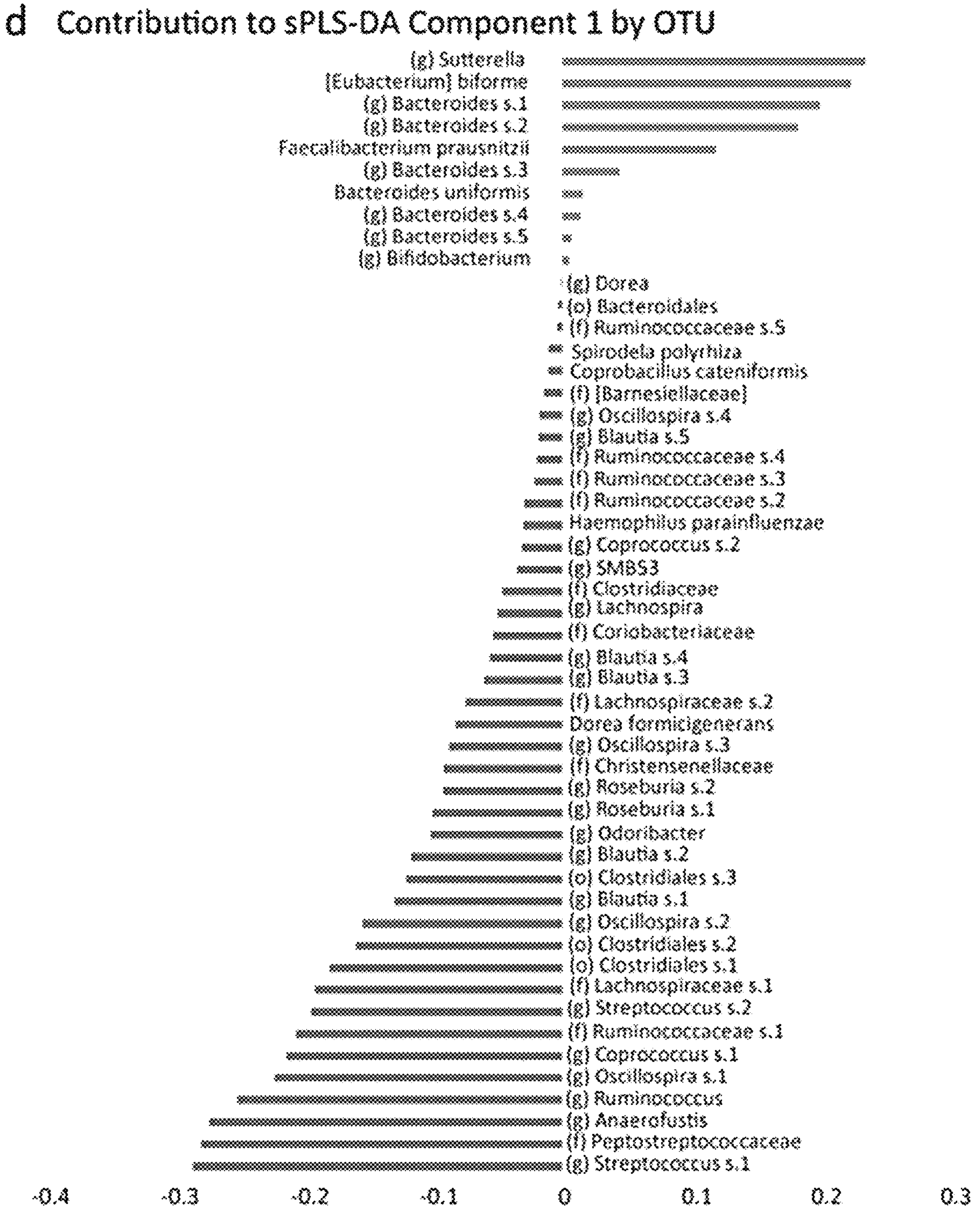
FIG. 7D shows contributing OTUs to the plot depicted in FIG. 7B.

Supervised learning methods were applied to identify a distinct microbial signature that differentiated between obese subjects and normal weight subjects without FA (FIGS. 7A & 7B) as well as obese subjects with or without FA (FIGS. 7C & 7D). Through the model, patients with normal BMIs were separated from patients with obesity by differences in OTUs belonging to such taxa as *Bacteroides*, Blautia, Lachnospiraceae, Ruminococcaceae, *Roseburia, Faecalibacterium* and *Clostridium*. In patients with obesity, over 30 different OTUs separated patients with FA from those without FA. Notable OTUs that distinguished patients without FA included *Eubacterium* biforme and *Bacteroides. Streptococcus* was the taxa with the largest contribution for obese subjects with FA.

Brain Reward Networks and Food Addiction

Figure 8A:
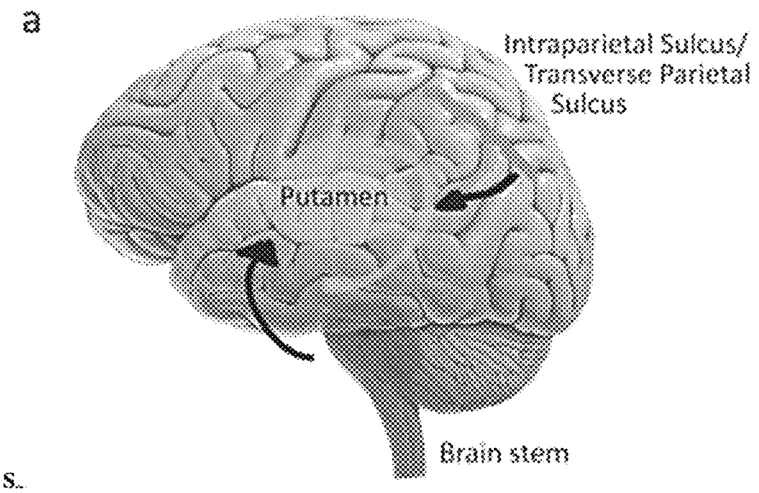
FIG. 8A is a schematic diagram of the significant brain region associated with food addiction. DTI pairwise studies showed that the communication between the intraparietal sulcus/transverse parietal (IntPS/TrPS) sulcus and brain stem to the putamen was positively associated with Food Addiction (FA) in patients with obesity.
Figure 8B:
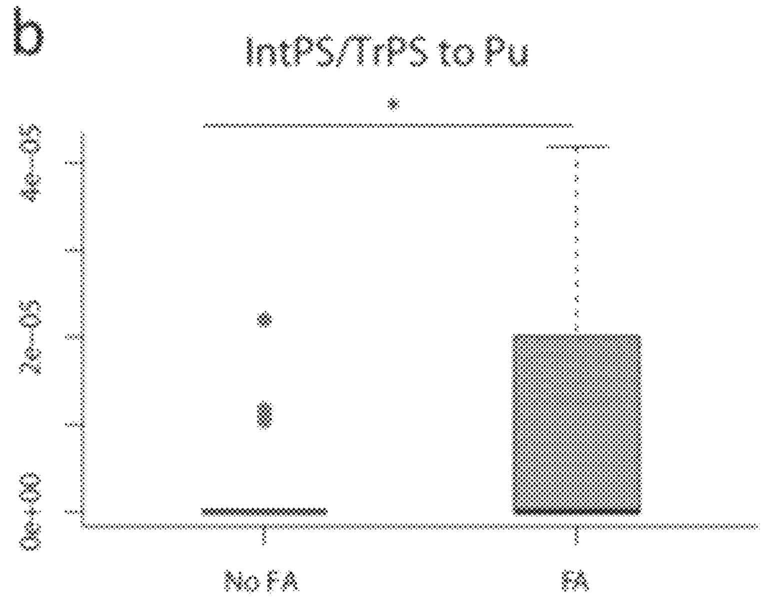
FIG. 8B shows the quantification of the studies in FIG. 8A. In particular.
Figure 8C:
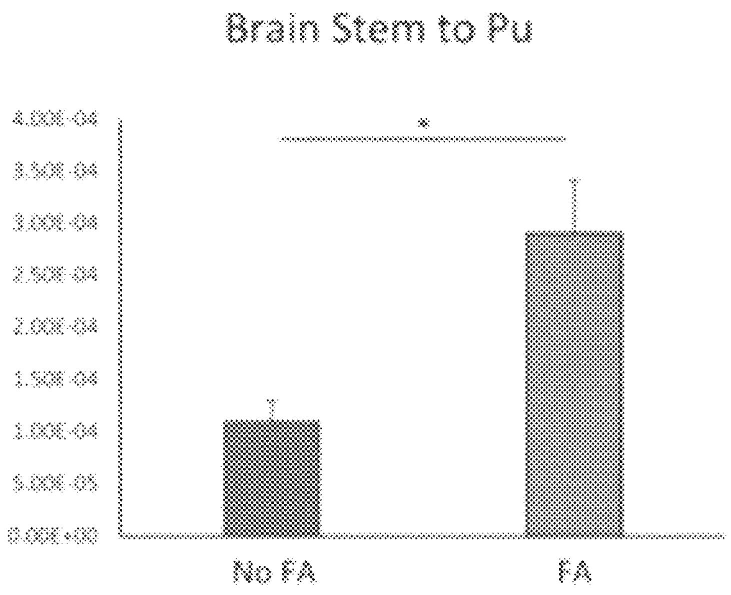
FIG. 8C shows the quantification of the studies in FIG. 8A. In particular.

DTI pairwise MRI showed greater anatomical connectivity between the putamen (a key reward region) and the brain stem (Cohen's d=1.12, p.adj value=0.0415) and intraparietal sulcus/transverse parietal sulcus (IntPS/TrPS) (Cohen's d=0.89, p.adj value=0.002) in obese subjects with FA compared to those subjects without FA (FIGS. 8A-C). Using DESEq2 analysis and dichotomizing the brain imaging data based on their respective median values, 17 OTUs were associated with an increase communication between the brain stem and the putamen (FIG. 8E). Similarly, 10 OTUs were associated with an increase communication between the putamen and the IntPS/TrPS (FIG. 8F). The OTU belonging to the genus *Megamonas* was positively associated with increase connectivity in both of these brain regions. Conversely, OTUs that belonged to *Bacteroides* and *Eubacterium* were negatively associated with the connections of both of these brain regions. *Akkermansia* was also negatively associated with the connection between the putamen and the IntPS/TrPS but was not associated with the connection between the putamen and the brain stem. There were no significant differences in DTI pairwise MRI brain imaging of patients with obesity without FA as compared to normal weight individuals. There were also no significant differences when comparing obese and overweight patients without FA to normal weight individuals.

Indolepropionate is Associated with Food Addiction

Figure 8D:
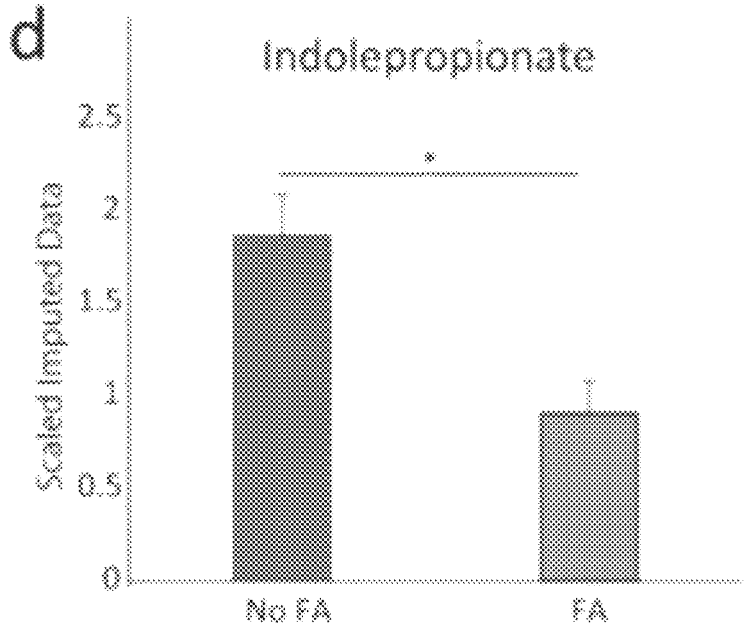
FIG. 8D shows the levels of fecal indolepropionate in obese subjects with or without FA.
Figure 8E:
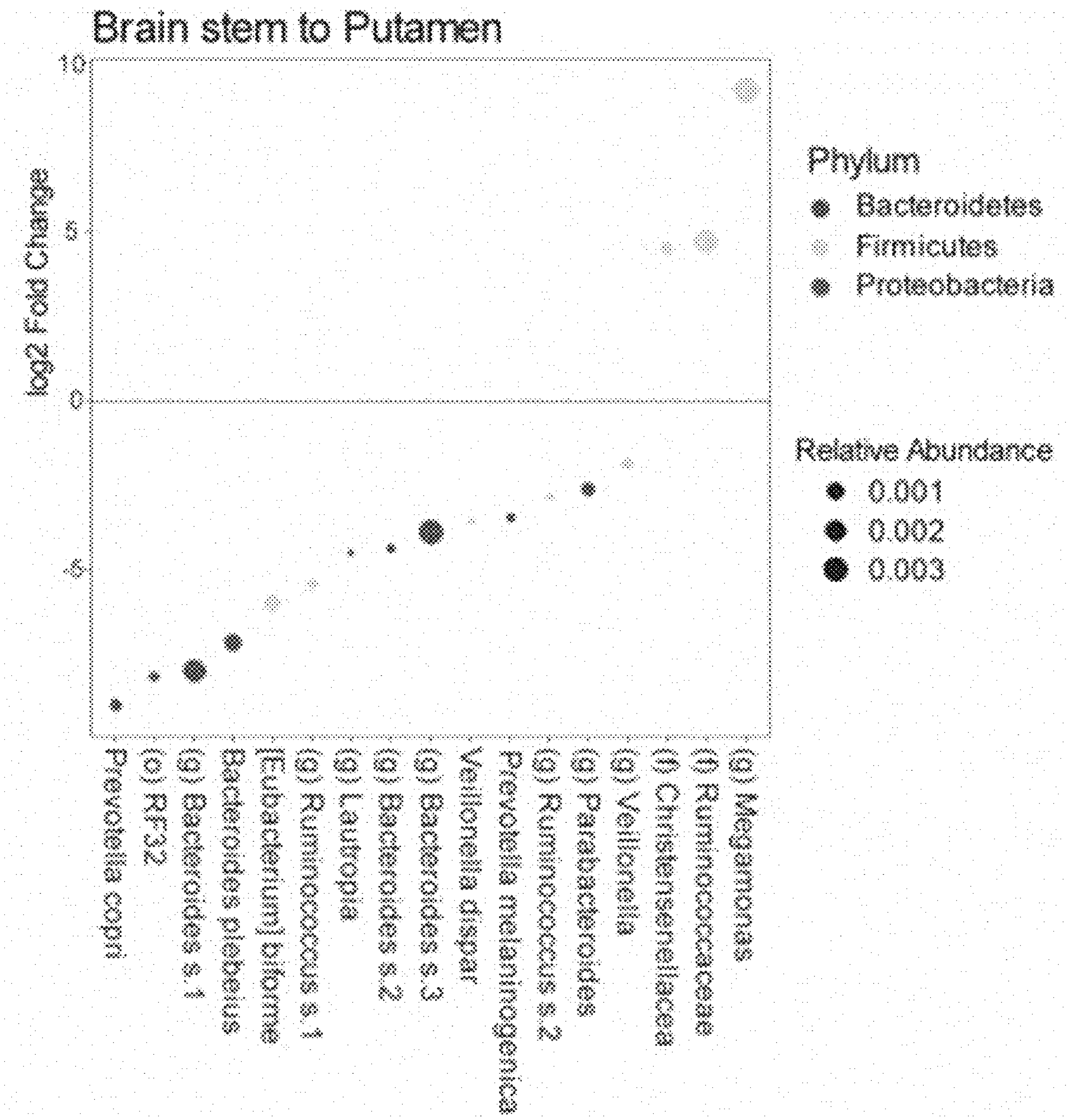
FIG. 8E depicts the results of DESEq2 analysis in obese subjects which showed several OTUs associated with increase connectivity between the brain stem and the putamen.
Figure 8F:
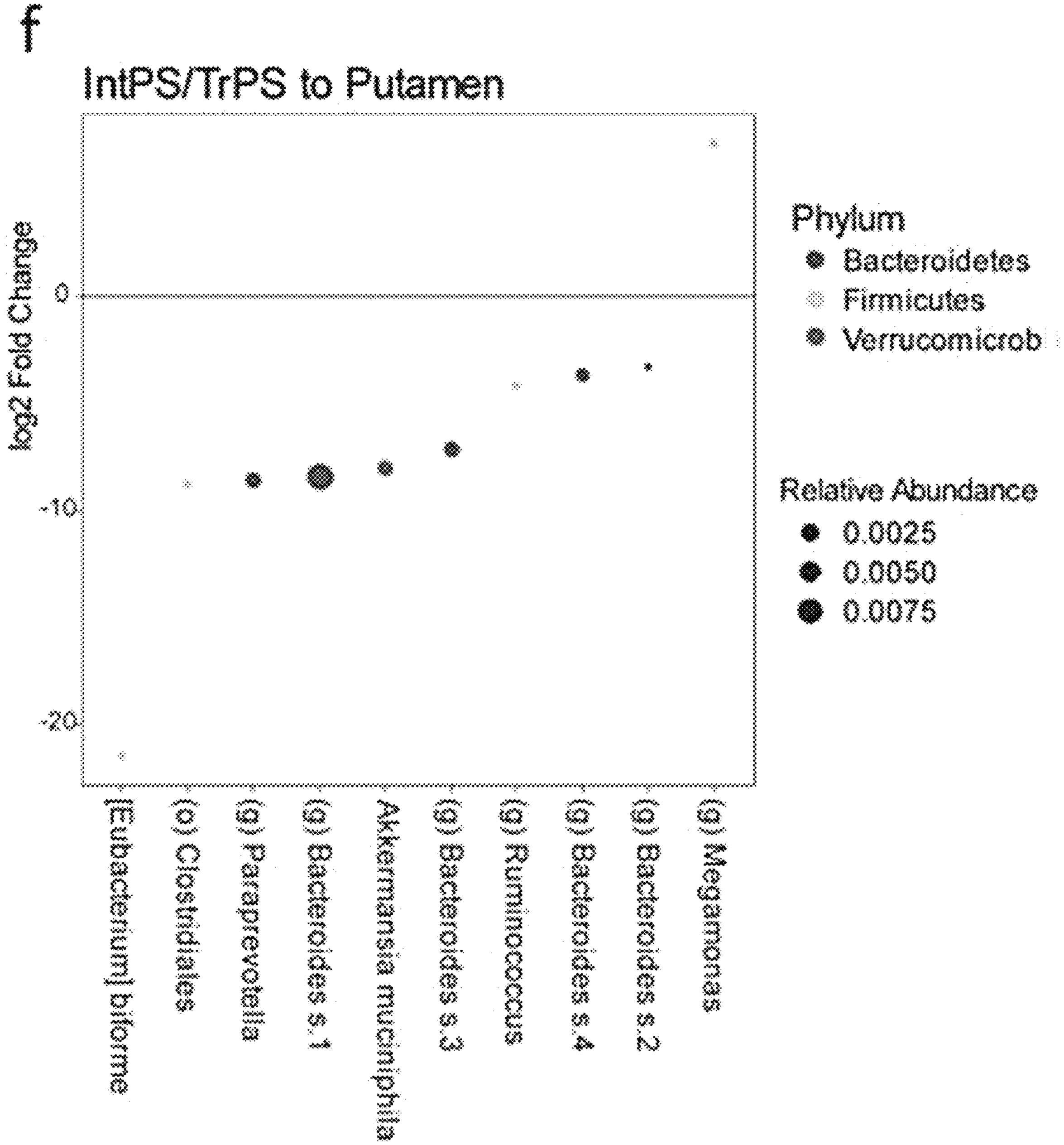
FIG. 8F depicts the results of DESEq2 analysis in obese subjects which showed several OTUs associated with increase connectivity between the IntPS/TrPS to the putamen.
Figure 8G:
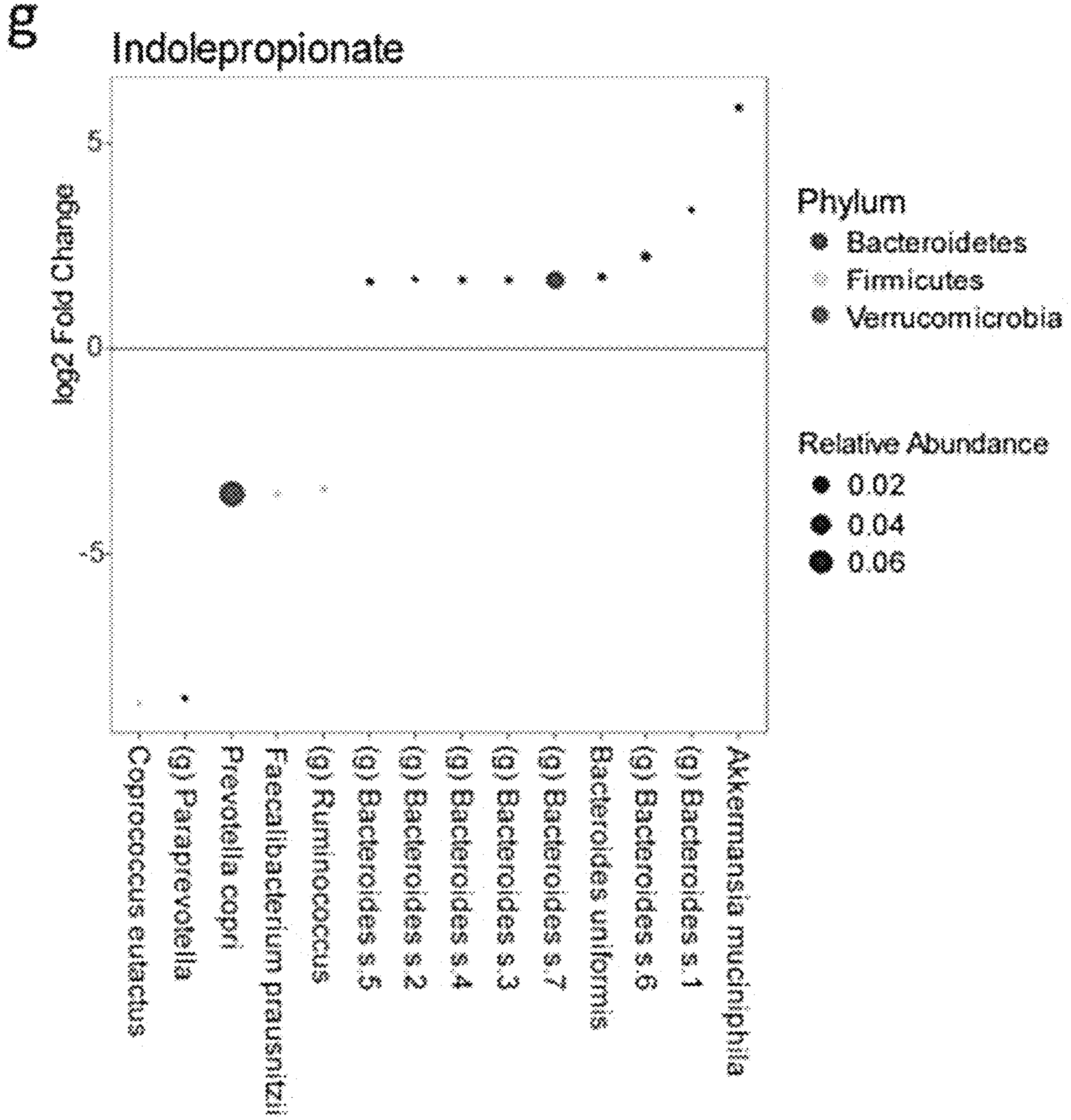
FIG. 8G shows the OTUs that are correlated to fecal indolepropionate by DESEq2 in patients with obesity. IntPS/TrPS: intraparietal sulcus/transverse parietal sulcus. Pu: Putamen

By analyzing fecal metabolites that were related to tryptophan metabolism, it was found that indolepropionate was negatively associated with FA in patients with obesity (Cohen's d, 0.74, p-value=0.045) (FIG. 8D). By analyzing the level of indolepropionate with fecal microbiome data, we discovered 14 OTUs that were correlated with indolepropionate (FIG. 8G). The highest abundant OTU that positively correlated to indolepropionate belonged to the genus *Bacteroides*. The highest abundant OTU that was negatively correlated to indolepropionate belonged to the genus *Prevotella*. All the OTUs that were positively associated with indolepropionate belonged to *Akkermansia* muciniphila and *Bacteroides*. There were no significant differences in fecal tryptophan metabolites of patients with obesity without FA as compared to normal weight individuals. There were also no significant differences in fecal metabolites when comparing obese and overweight patients without FA to normal weight individuals.

Figure 9A:
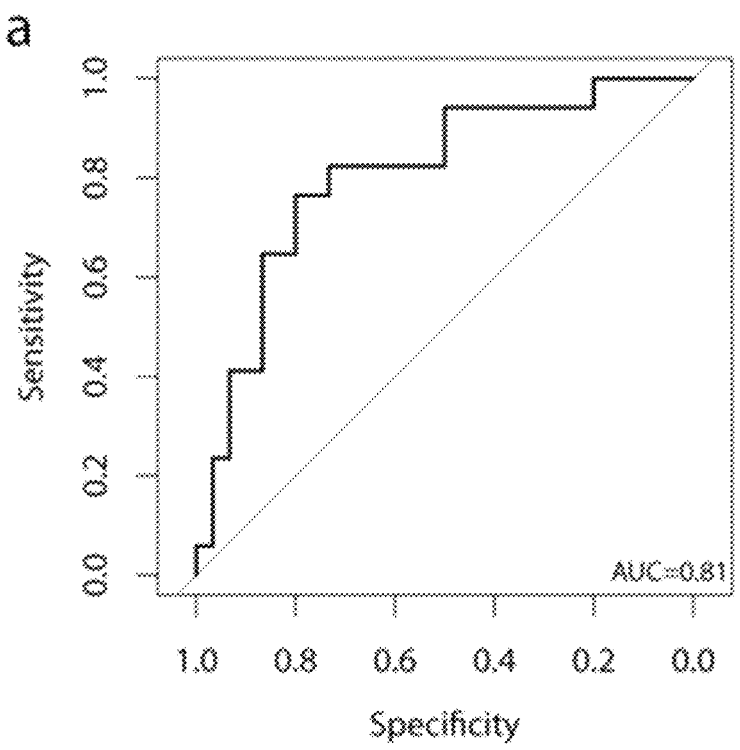
FIG. 9A shows a ROC curve for the random forest classifier (AUCROC=0.81) which depicts that combining fecal metabolite with 16S and brain imaging data results in a highly accurate classifier that identifies subjects with food addiction (FA).
Figure 9B:
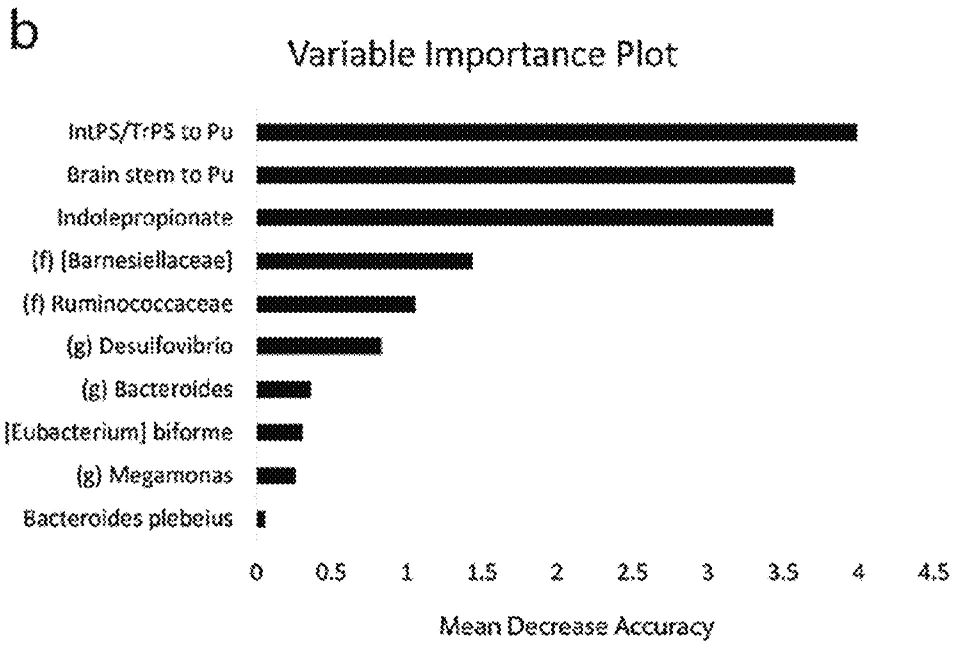
FIG. 9B is a variable importance plot of each factor on the accuracy of the classifier discussed in FIG. 9A. IntPS/TrPS: intraparietal sulcus/transverse parietal sulcus. Pu: Putamen.

Random Forest Classifier Based on Brain Imaging, Fecal Metabolite, and 16S Sequencing Accurately Identifies Subjects with Food Addiction Using the significant findings of the brain imaging, fecal metabolite, and DESEq2 analysis of the fecal microbiome, a random forest classifier was created with a high accuracy for predicting obese subjects with FA behaviors. The AUC in 5-fold cross-validation was 0.81 (FIG. 9A). The contribution of each variable was expressed with a variable importance score, which measures the decrease in accuracy of the classifier if that feature was removed. The variables with the highest scores were those pertaining to brain imaging and indolepropionate. Seven OTUs also contributed significantly to the classifier and those OTUs belonged to Barnesiellaceae, Ruminococcaceae, *Desulfovibrio, Bacteroides, Eubacterium*, and *Megamonas* (FIG. 9B).

TABLE 1

Exemplary Compounds of the Present Invention

| | No Food Addiction (No FA) (n = 86) | Food Addiction (FA) (n = 19) | p-value |
|---|---|---|---|
| Age (mean +/− SD) (yrs) | 33.19 ± 10.31 | 28.57 ± 8.66 | 0.07 |
| BMI (mean +/− SD) | 29.1 ± 5.4 | 35.6 ± 5.3 | 0.0001 |
| Normal Weight (n = 16) % | 18.60 | 0.00 | 0.0001 |
| Overweight (n = 38) % | 41.86 | 10.52 | |
| Obese (n = 51) % | 39.53 | 89.47 | |
| YFAS Symptom Count (mean +/− SD) | 1.15 ± 0.77 | 3.63 ± 1.16 | <0.0001 |
| | Race/Ethnicity | | |
| Hispanic (n = 41) % | 36.05 | 52.63 | 0.55 |
| Caucasian (n = 28) % | 23.26 | 42.11 | |
| African American (n = 13) % | 12.79 | 10.53 | |
| Asian (n = 21) % | 20.93 | 15.79 | |
| Other (n = 2) % | 2.33 | 0 | |

DISCUSSION

Disclosed herein is a study which utilize a systems biology approach to demonstrate associations between FA and changes in brain-gut-microbiome interactions by analyzing fecal microbes, metabolites, and anatomical connectivity (DTI) brain data. FA behaviors in females were associated with a distinct microbial profile, increased connectivity with the putamen of the reward center of the brain, and a decrease in indolepropionate, a tryptophan derived microbial metabolite.

The study results indicated a strong negative association between *Bacteroides, Akkermansia*, and *Eubacterium* with FA. *Bacteroides* is the major genus belonging to the phylum Bacteroidetes. In both human and mouse studies, a rise in Bacteroidetes is often associated with a leaner phenotype. In bariatric studies, subjects that had the most significant weight loss were those that had higher levels of *Bacteroides* and lower levels of *Prevotella*. In a prospective study, *Bacteroides* species were higher in lean individuals and those subjects who were able to achieve weight loss as compared to subjects with obesity. Whether the associations noted between *Bacteroides* and obesity are causative is still an area of active research. In the data herein, *Bacteroides* was positively associated with indolepropionate and negatively associated with brain regions related to FA.

*Akkermansia* was also another genus that was significantly associated with FA, brain imaging, and fecal metabolites. *Akkermansia* is a mucin-degrading bacterium that has been extensively studied for its protective role in metabolic syndrome and insulin sensitivity both in human and mouse studies. In a study of 41 females with obesity undergoing calorie restriction, an increase in relative abundance of *Akkermansia* was associated with improved fasting glucose, waist-to-hip ratio, and subcutaneous adipocyte diameter. This led to a recent phase 1 randomized double-blind, placebo-controlled clinical trial showing that *Akkermansia* supplementation in obese/overweight volunteers led to improved insulin sensitivity, reduced plasma cholesterol, and a trend towards decreased body weight and fat mass.

However, unlike *Akkermansia* and *Bacteroides, Eubacterium biforme* has not been as well studied with regards to obesity or metabolic syndrome. In our study we show *Eubacterium* to be negatively associated with FA as well as key areas of the brain reward network. Similar to *Bacteroides, Eubacterium* is known to be a significant producer of short-chain fatty acids. Short-chain fatty acids is the by-product of bacterial fermentation of indigestible dietary fiber. The most abundant short-chain fatty acid is butyrate and several animal studies have shown that butyrate can be protective against obesity by increasing GLP-1, leptin release, and increasing fatty acid oxidation. Butyrate is also able to communicate directly with the central nervous system by crossing the blood-brain barrier and activating the vagus nerve and hypothalamus. (28)

While *Akkermansia, Bacteroides*, and *Eubacterium* were negatively associated with FA, *Megamonas* was one of the few bacteria that was both positively associated with FA and an increased activity of the reward network of the brain. In human studies, *Megamonas* has been associated with an increase prevalence of prediabetes and childhood obesity. In context, these associations between the gut microbiome and obesity may be mediated through interactions involving the gut-brain axis.

In the study disclosed herein, it was observed that alpha diversity did not differ between subjects with or without FA but it was seen that alpha diversity did differ by race and ethnicity, which may be a reflection of dietary differences across these groups. Larger samples, will allow for future analyses to account for cultural factors and for race and ethnicity differences.

Analysis of fecal metabolites revealed a negative association between indolepropionate and FA. Microbial analysis showed that *Bacteroides* and *Akkermansia* was positively correlated with indolepropionate while bacteria belonging to the phylum Firmicutes were negatively associated. This finding is in line with the numerous studies that have shown an increase in Firmicutes and a decrease in *Bacteroides* in patients with diabetes, metabolic syndrome and obesity. Indolepropionate belongs to a larger class of tryptophan-derived metabolites termed “indoles.” In contrast to other tryptophan derived metabolites (serotonin, kynurenine), which have also been implicated in brain-gut-microbiome interactions in obesity, indoles are the result of exclusively microbial metabolism, in which most undigested dietary tryptophan in the gut is converted to indoles. The results presented herein are consistent with previously published work, where the associations between indoles on key regions of the extended reward network and both obesity and FA is described. Indoles play an important role in modulating kynurenine synthesis, reducing central nervous system inflammation, improving the mucosal intestinal barrier, and altering GLP-1 secretion—all of which have been shown to be disrupted in states of obesity. Although indolepropionate has been less extensively studied, previous work has demonstrated a neuroprotective role of indolepropionate against Alzheimer’s disease and neural oxidative stress. Furthermore, a Finnish study of 200 subjects showed that a higher level of serum indolepropionate acid was associated with a reduce risk of type 2 diabetes. This data suggests that indolepropionate may have both local protective effects on intestinal barrier function as well as remote effects on preserving β-cell function and central nervous system inflammation.

This study also demonstrated that that decreased fecal indolepropionate was associated with not only increased FA behaviors, but that this was related to increased connectivity between key reward regions involving the putamen. In line with the previous fecal microbiome data in FA and indolepropionate, a negative association of *Bacteroides* and *Akkermansia* to the connectivity between the putamen and the intraparietal sulcus was observed. Normal eating behavior is under the control of the brain’s homeostatic system and hedonic system, which includes regions involved in the processing of food-seeking behavior, inhibition, and integrating information to make decisions regarding food intake. However, in both FA and obesity, activity within the extended reward network can override the homeostatic system. This dominance of hedonic over homeostatic influences on eating behavior has been related to the ubiquitous presence of cheap, highly palatable, high caloric foods, which are enhanced for taste and salience. This hedonic dominance not only leads to increases in cravings and ingestion of these foods, but environmental factors such as stress and adversity can serve as conditional cues for future food intake and long-term weight gain. Some studies have indicated that overconsumption of highly palatable foods rich in calories, fat, and sugar reduce the reward thresholds of such foods when ingested, and therefore require a higher intake to generate the same satisfaction.

Integrating the significant findings on brain imaging, fecal metabolites, and the fecal microbiome, we created a random forest classifier, which demonstrated a high accuracy for predicting obese individuals with FA behaviors. Next to indolepropionate and connectivity of key reward network region (the putamen), the bacterial genera with significant contribution to the classifier that were also significant in other analysis belonged to *Bacteroides, Eubacterium*, and *Megamonas*.

There are several limitations to our study. Because of the cross-sectional design the results only show associations between behavior, gut microbiome and brain structure. However, in the absence of a truly valid food addiction model in animals and the challenges of doing studies in humans that address the bidirectional BGM interactions, cross sectional studies are essential first steps to identify correlations within the BGM axis in humans. Another limitation is that this study enrolled only females, and due to the lower prevalence rates of FA in males compared to females, it would require larger sample sizes to observe the same effects in males. Lastly, this data should be validated in an external cohort to confirm the accuracy of the classifier.

Figure 10:
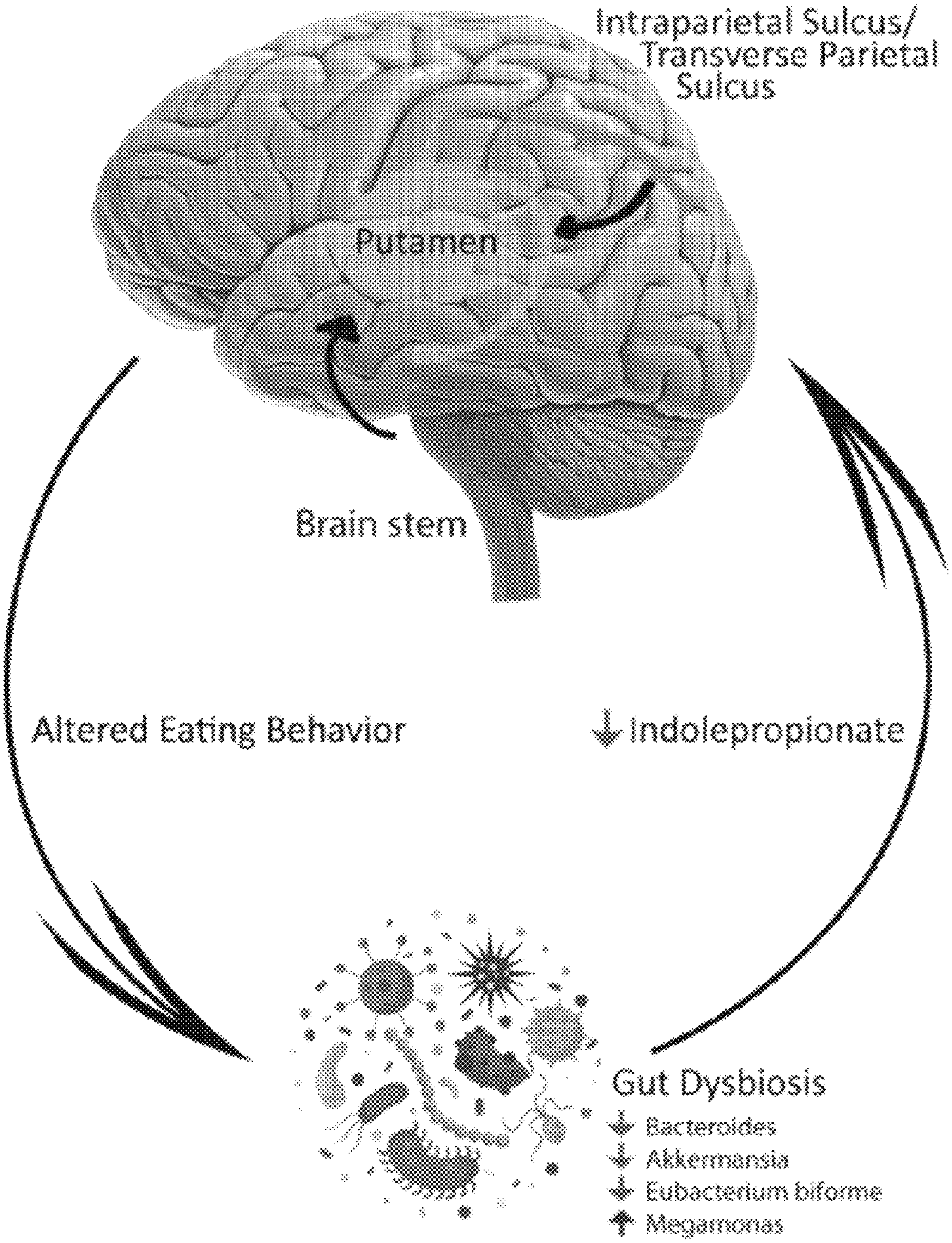
FIG. 10 is a schematic diagram showing that the gut microbiome to food addiction (FA) via changes in metabolite and changes in connectivity of the brain's reward system.

In conclusion, food addiction refers to maladaptive ingestive behaviors resulting from a shift from primarily homeostatic to hedonic regulatory mechanisms of food intake which primarily occurs in individuals with obesity. This shift reflects alterations at all levels of the BGM axis. The results of this study suggest that FA behavior may be mediated via effects of the gut microbiome and their metabolites on the reward centers of the brain (FIG. 10).

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A pharmaceutical composition comprising at least one bacterial strain from the genus of *Akkermansia*, at least one bacterial strain from the genus *Bacteroides*, a pharmaceutically acceptable excipient, and a compound, wherein the compound is

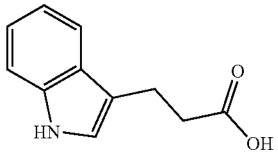 [SMILES: O=C(O)CCc1c[nH]c2ccccc12]

(indole-3-propanoic acid) or a salt thereof.

2. The composition of claim 1, wherein the bacterial strain further comprises *Bacteroides*.

3. The composition of claim 1, wherein the bacterial strain further comprises *Clostridiales*.

4. The composition of claim 1, wherein the bacterial strain further comprises *Faecalibacterium*.

5. The composition of claim 1, wherein the bacterial strain further comprises *Faecalibacterium prausnitzii*.

6. The composition of claim 1, wherein the bacterial strain further comprises *Ruminoccoccus*.

7. A food supplement comprising at least one bacterial strain from the genus *Akkermansia*, at least one bacterial strain from the genus *Bacteroides*, and a compound, wherein the compound is

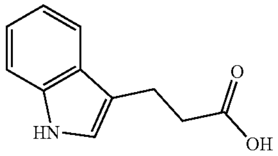 [SMILES: O=C(O)CCc1c[nH]c2ccccc12]

(indole-3-propanoic acid) or a salt thereof.

8. The food supplement of claim 7, wherein the food supplement comprises *Akkermansia muciniphila*.

9. The food supplement of claim 7, wherein the bacterial strain further comprises *Bacteroides*.

10. The food supplement of claim 7, wherein the bacterial strain further comprises *Clostridiales*.

11. The food supplement of claim 7, wherein the bacterial strain further comprises *Faecalibacterium*.

12. The food supplement of claim 7, wherein the bacterial strain further comprises *Faecalibacterium prausnitzii*.

13. The food supplement of claim 7, wherein the bacterial strain further comprises *Ruminoccoccus*.

14. A method of treating obesity in a subject, comprising administering to a subject in need thereof the food supplement of claim 7.

15. The method of claim 14, wherein the subject has an increased number of bacteria from a bacterial strain selected from the genus of *Megamonas* as compared to an individual with a healthy weight.

* * * * *